(12) United States Patent
Pilkington et al.

(10) Patent No.: US 10,545,048 B2
(45) Date of Patent: Jan. 28, 2020

(54) MEDICATION DISPENSING DEVICE AND METHODS

(71) Applicant: CARDINAL HEALTH COMMERICAL TECHNOLOGIES, LLC, Dublin, OH (US)

(72) Inventors: Mark Allen Pilkington, Powell, OH (US); Benjamin Eli Stormer, Worthington, OH (US); Daniel Lee Michael, Aurora, OH (US); Jason R Ertel, Twinsburg, OH (US); Vikki Nowak, Cleveland Heights, OH (US)

(73) Assignee: Cardinal Health Commercial Technologies, LLC, Dublin, OH (US)

( * ) Notice: Subject to any disclaimer, the term of this patent is extended or adjusted under 35 U.S.C. 154(b) by 289 days.

(21) Appl. No.: 15/216,385

(22) Filed: Jul. 21, 2016

(65) Prior Publication Data

US 2017/0074717 A1   Mar. 16, 2017

Related U.S. Application Data

(60) Provisional application No. 62/196,131, filed on Jul. 23, 2015, provisional application No. 62/196,165, filed on Jul. 23, 2015.

(51) Int. Cl.
*A61J 7/00* (2006.01)
*G01G 21/22* (2006.01)
(Continued)

(52) U.S. Cl.
CPC .............. *G01G 19/415* (2013.01); *A61J 1/05* (2013.01); *A61J 7/0069* (2013.01); *A61J 7/0084* (2013.01);
(Continued)

(58) Field of Classification Search
CPC .. G01G 19/4144; G01G 19/415; G01G 21/22; G01G 23/3728; A61J 2200/74;
(Continued)

(56) References Cited

U.S. PATENT DOCUMENTS

D273,093 S    3/1984  Lunden
D274,040 S    5/1984  Ridgley
(Continued)

FOREIGN PATENT DOCUMENTS

WO    2013127564 A1    9/2013
WO    2014165206 A1   10/2014

*Primary Examiner* — Natalie Huls
(74) *Attorney, Agent, or Firm* — McDonnell Boehnen Hulbert & Berghoff LLP

(57) ABSTRACT

A medication dispensing device may include a plurality of trays, each tray optionally including a load cell configured to measure a mass/weight of a medication contained in the respective tray. Each tray is placeable in a medication accessible position and a medication inaccessible position. The medication dispensing device includes a user interface configured to provide instructions and/or other information with regard to access for each medication. A processor provides instructions to selectively place each tray in the medication accessible position, and to determine, based on any change in the mass of the medication placed in the medication accessible position, whether the appropriate amount of the medication is removed from the tray.

16 Claims, 19 Drawing Sheets

(51) Int. Cl.
*G01G 23/37* (2006.01)
*A61J 7/04* (2006.01)
*G01G 19/415* (2006.01)
*A61J 1/05* (2006.01)
*G06F 19/00* (2018.01)
*G16H 40/63* (2018.01)
*G01G 19/414* (2006.01)

(52) U.S. Cl.
CPC ........ *A61J 7/0481* (2013.01); *G01G 19/4144* (2013.01); *G01G 21/22* (2013.01); *G01G 23/3728* (2013.01); *G06F 19/00* (2013.01); *G06F 19/3462* (2013.01); *G16H 40/63* (2018.01); *A61J 2200/30* (2013.01); *A61J 2200/74* (2013.01); *A61J 2205/10* (2013.01); *A61J 2205/60* (2013.01)

(58) Field of Classification Search
CPC . A61J 2205/10; A61J 7/0069; G06F 19/3462; G16H 40/63
See application file for complete search history.

(56) References Cited

U.S. PATENT DOCUMENTS

| | | | |
|---|---|---|---|
| D279,864 S | 7/1985 | Ridgley | |
| 5,011,018 A | 4/1991 | Keffeler | |
| D356,904 S | 4/1995 | Wolff | |
| 5,735,406 A | 4/1998 | Keffeler | |
| 5,752,621 A | 5/1998 | Passamante | |
| 5,774,865 A * | 6/1998 | Glynn | G01G 19/414 705/2 |
| 5,852,590 A | 12/1998 | De La Huerga | |
| D408,625 S | 4/1999 | Barker | |
| 6,042,858 A | 3/2000 | Kairys | |
| 6,150,942 A | 11/2000 | O'Brien | |
| 6,259,654 B1 | 7/2001 | De la Huerga | |
| 6,294,999 B1 * | 9/2001 | Yarin | A61J 7/0481 340/573.1 |
| 6,380,858 B1 | 4/2002 | Yarin et al. | |
| D459,987 S | 7/2002 | Christianson | |
| 6,529,446 B1 | 3/2003 | De la Huerga | |
| 6,615,107 B2 * | 9/2003 | Hubicki | A61J 7/0481 700/237 |
| 6,636,780 B1 * | 10/2003 | Haitin | A61G 12/001 221/2 |
| 6,663,846 B1 | 12/2003 | McCombs et al. | |
| 6,702,146 B2 | 3/2004 | Varis | |
| 6,717,598 B1 | 4/2004 | Melton, Jr. et al. | |
| 6,771,174 B2 * | 8/2004 | Broas | A61J 7/0481 340/573.1 |
| 6,973,371 B1 | 12/2005 | Benouali | |
| 6,985,869 B1 | 1/2006 | Stoll et al. | |
| 7,002,476 B2 | 2/2006 | Rapchak | |
| 7,072,738 B2 | 7/2006 | Bonney et al. | |
| 7,097,037 B1 | 8/2006 | Keffeler et al. | |
| 7,126,879 B2 | 10/2006 | Snyder | |
| 7,151,456 B2 | 12/2006 | Godfrey | |
| 7,170,823 B2 | 1/2007 | Fabricius et al. | |
| 7,269,476 B2 | 9/2007 | Ratnakar | |
| D555,893 S | 11/2007 | Mulaw | |
| 7,304,582 B2 | 12/2007 | Kerr et al. | |
| 7,369,919 B2 * | 5/2008 | Vonk | A61J 7/0481 700/242 |
| 7,395,929 B2 | 7/2008 | Keffeler et al. | |
| 7,424,888 B2 | 9/2008 | Harvey et al. | |
| 7,451,876 B2 | 11/2008 | Bogash et al. | |
| D588,355 S | 3/2009 | Muehlhausen et al. | |
| D597,203 S | 7/2009 | Tauer | |
| D606,736 S | 12/2009 | Coran | |
| D609,592 S | 2/2010 | Reid | |
| 7,793,785 B2 * | 9/2010 | Keffeler | A61J 1/03 206/532 |
| 7,801,745 B2 | 9/2010 | Walker et al. | |
| 7,821,404 B2 | 10/2010 | Walker et al. | |
| D627,062 S | 11/2010 | Tanguay | |
| 7,828,147 B2 | 11/2010 | Caracciolo et al. | |
| 7,844,361 B2 | 11/2010 | Jean-Pierre | |
| 7,926,850 B1 | 4/2011 | Muncy et al. | |
| 7,928,835 B1 | 4/2011 | Jovanov et al. | |
| 7,945,461 B2 | 5/2011 | Sekura | |
| D640,050 S | 6/2011 | Barrass | |
| 7,956,727 B2 | 6/2011 | Loncar | |
| 7,978,564 B2 * | 7/2011 | De La Huerga | A61M 5/14212 221/15 |
| D643,618 S | 8/2011 | Guichet | |
| 7,996,243 B1 | 8/2011 | Ali et al. | |
| D645,559 S | 9/2011 | Green et al. | |
| 8,014,232 B2 | 9/2011 | Niemiec et al. | |
| 8,019,471 B2 | 9/2011 | Bogash et al. | |
| 8,032,393 B2 | 10/2011 | Nadas et al. | |
| 8,055,509 B1 | 11/2011 | Walker et al. | |
| 8,068,931 B2 | 11/2011 | Tran et al. | |
| 8,069,056 B2 | 11/2011 | Walker et al. | |
| D650,986 S | 12/2011 | Brady et al. | |
| 8,085,135 B2 | 12/2011 | Alloro et al. | |
| 8,108,068 B1 | 1/2012 | Boucher et al. | |
| 8,147,381 B2 | 4/2012 | Iwashita et al. | |
| 8,149,096 B2 | 4/2012 | Metry et al. | |
| D662,217 S | 6/2012 | Brown et al. | |
| 8,262,394 B2 | 9/2012 | Walker et al. | |
| D670,377 S | 11/2012 | Adams | |
| D672,457 S | 12/2012 | Foley | |
| D674,482 S | 1/2013 | Wurapa | |
| 8,423,181 B2 | 4/2013 | Hallin | |
| 8,424,517 B2 | 4/2013 | Sutherland et al. | |
| 8,536,987 B2 | 9/2013 | Metry et al. | |
| 8,581,709 B2 | 11/2013 | Mazur | |
| 8,583,281 B2 | 11/2013 | Bear et al. | |
| 8,600,548 B2 | 12/2013 | Bossi et al. | |
| 8,725,291 B2 | 5/2014 | Czaja et al. | |
| 8,754,769 B2 * | 6/2014 | Stein | A61J 7/0409 340/540 |
| D710,126 S | 8/2014 | Salonen | |
| D710,701 S | 8/2014 | Lai | |
| D711,195 S | 8/2014 | Cornu et al. | |
| 8,800,071 B2 | 8/2014 | Sanchez et al. | |
| 8,805,577 B2 | 8/2014 | Buisman et al. | |
| D715,041 S | 10/2014 | McMillen | |
| 8,884,752 B2 * | 11/2014 | Tai | G06Q 50/24 340/539.12 |
| D718,922 S | 12/2014 | Lai | |
| D718,923 S | 12/2014 | Lai | |
| D719,344 S | 12/2014 | Miller et al. | |
| 8,914,148 B2 | 12/2014 | Wagner | |
| D727,482 S | 4/2015 | Brathwaite | |
| D737,959 S | 9/2015 | Wilson | |
| D746,979 S | 1/2016 | Dominguez I et al. | |
| D748,751 S | 2/2016 | Stallings | |
| D761,551 S | 7/2016 | Stueckemann et al. | |
| D765,389 S | 9/2016 | Martin | |
| D767,297 S | 9/2016 | Madsen et al. | |
| 9,501,625 B2 * | 11/2016 | Tsai | G06F 19/00 |
| D773,175 S | 12/2016 | Fagen | |
| D781,065 S | 3/2017 | Brownley et al. | |
| 9,597,261 B2 | 3/2017 | Baarman et al. | |
| 2005/0178786 A1 | 8/2005 | Raines | |
| 2006/0058724 A1 | 3/2006 | Handfield et al. | |
| 2006/0154642 A1 | 7/2006 | Scannell | |
| 2006/0259188 A1 | 11/2006 | Berg | |
| 2009/0012818 A1 * | 1/2009 | Rodgers | G01G 17/00 705/3 |
| 2010/0076595 A1 | 3/2010 | Nguyen | |
| 2010/0185456 A1 | 7/2010 | Kansal | |
| 2011/0187549 A1 * | 8/2011 | Balasingam | A47B 81/00 340/687 |
| 2013/0030566 A1 * | 1/2013 | Shavelsky | A61J 7/04 700/244 |
| 2013/0191140 A1 | 7/2013 | Fotheringham et al. | |
| 2013/0313311 A1 | 11/2013 | Fath et al. | |
| 2014/0055588 A1 | 2/2014 | Bangera et al. | |
| 2014/0207278 A1 * | 7/2014 | Czaja | G06F 19/3456 700/240 |

(56) References Cited

U.S. PATENT DOCUMENTS

| | | |
|---|---|---|
| 2014/0260985 A1 | 9/2014 | Akdogan et al. |
| 2014/0262918 A1 | 9/2014 | Chu |
| 2014/0263391 A1 | 9/2014 | Akdogan et al. |
| 2014/0263423 A1 | 9/2014 | Akdogan et al. |
| 2014/0263425 A1 | 9/2014 | Akdogan et al. |
| 2014/0267719 A1 | 9/2014 | Akdogan et al. |
| 2014/0277705 A1* | 9/2014 | Czaja ............... G06F 19/00 700/237 |
| 2014/0277707 A1 | 9/2014 | Akdogan et al. |
| 2014/0277710 A1 | 9/2014 | Akdogan et al. |
| 2014/0278508 A1 | 9/2014 | Akdogan et al. |
| 2016/0015602 A1* | 1/2016 | Panzini ............ A61J 7/0481 206/534 |

\* cited by examiner

MEDICATION DISPENSING DEVICE AND METHODS

RELATED APPLICATIONS

This application claims priority to U.S. Provisional Patent Application No. 62/196,131, filed on Jul. 23, 2015, titled "MEDICATION DISPENSING DEVICE AND METHODS" and U.S. Provisional Patent Application No. 62/196,165, filed on Jul. 23, 2015, titled "MEDICATION DISPENSING DEVICE AND METHODS". The entirety of each of these applications is hereby incorporated by reference.

BACKGROUND

Patients may be prescribed multiple medications to treat various conditions. Additionally, patients may regularly take non-prescription drugs (e.g., aspirin) or supplements. Accordingly, some patients may need to manage a regimen involving multiple medications.

Current medication management solutions such as pill sorters still require the patients or caregivers to manually sort and track medications. Compliance with a complicated medication regimen may be difficult for patients. Further, care providers may not know whether a patient is complying with a medication regimen, which may affect the ability of the care provider to assess the effectiveness of the medication regimen.

In view of the foregoing, as well as other factors, there remains a need for improvements over current medication dispensing procedures.

SUMMARY

The following presents a simplified summary of one or more aspects in order to provide a basic understanding of such aspects. This summary is not an extensive overview of all contemplated aspects, and is intended to neither identify key or critical elements of all aspects nor delineate the scope of any or all aspects. Its sole purpose is to present some concepts of one or more aspects in a simplified form as a prelude to the more detailed description that is presented later.

The disclosure provides for a medication dispensing device. The medication dispensing device may include a plurality of trays, each tray including a load cell configured to measure a mass of a medication (e.g., by weight) contained in the respective tray. Each tray is placeable in a medication accessible position and a medication inaccessible position. The medication dispensing device may include a user interface configured to provide instructions with regard to access for each medication. A processor may be configured to provide instructions to selectively place each tray in the medication accessible position, and to determine, based on any change in the mass/weight of the medication placed in the medication accessible position, whether any amount of the medication is removed from the tray. The disclosure also provides methods for loading medication into the medication dispensing device and dispensing medication from the medication dispensing device.

In an aspect, the disclosure provides a medication dispensing device. The medication dispensing device includes a plurality of trays, each tray including mass/weight measurement features, such as a load cell configured to measure the mass/weight of a medication contained in the respective tray, each tray being placeable in a medication accessible position (e.g., the tray being open to access) and a medication inaccessible position (e.g., the tray being closed to access). The medication dispensing device further may include a user interface configured to provide instructions with regard to access for each medication. The medication dispensing device may also include a processor configured to provide instructions to selectively place each tray in the medication accessible position and determine, based on any change in the mass/weight of the medication placed in the medication accessible position, whether any amount of the medication is removed from the tray.

In another aspect, the disclosure provides a medication container. The medication container may include a bowl portion having an outer edge in a first plane. In one example implementation, the outer edge may include a first convex arc segment, a second concave arc segment concentric with the first convex arc segment, and two straight segments connecting respective ends of the first convex arc segment and the second concave arc segment. The length of the first convex arc segment may be greater than a length of the second concave arc segment. A bottom surface of the bowl may be sloped such that the bowl is shallower near the first convex segment than near the second concave arc segment. The medication container may further include a movable lid forming a press fit with the outer edge of the bowl.

In another aspect, the disclosure provides a method of dispensing medication. The method may include receiving medication information for medication to be dispensed from a dispensing device, the medication information including a prescribed medication mass/weight. The method may further include prompting a user to insert the medication into a tray. The method may also include determining a mass/weight of the medication to determine an actual medication mass/weight. The method may additionally include determining whether the actual medication mass/weight matches the prescribed medication mass/weight.

Additional advantages and novel features of these aspects will be set forth in part in the description that follows, and in part will become more apparent to those skilled in the art upon examination of the following or upon learning by practice thereof.

BRIEF DESCRIPTION OF THE DRAWINGS

The disclosed aspects will hereinafter be described in conjunction with the appended drawings, provided to illustrate example features and not to limit the disclosed aspects, wherein like designations denote like elements, and in which.

DETAILED DESCRIPTION

Various aspects are now described with reference to the drawings. In the following description, for purposes of explanation, numerous specific example details are set forth in order to provide a thorough understanding of one or more aspects. It may be evident, however, that such aspects may be practiced without these specific details.

Figure 1:
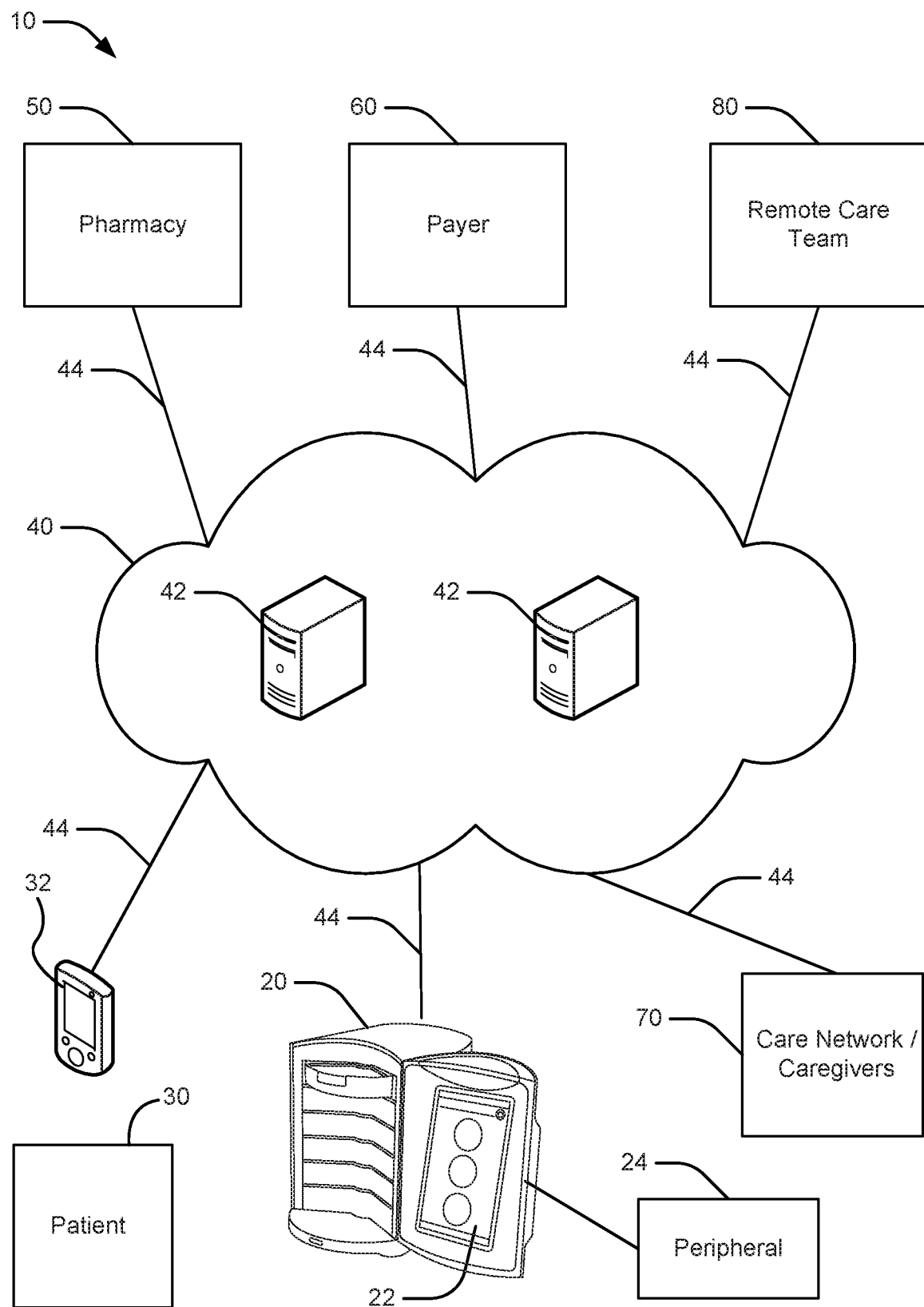
FIG. 1 illustrates a system including a medication dispensing device in accordance with aspects of the present disclosure.

FIG. 1 illustrates an example system 10 including an example medication dispensing device 20. The system 10 may provide a wellness solution for managing a various aspects of a patient's health such as medications, testing, subjective evaluation, communications, and appointments. The medication dispensing device 20 may store medications (e.g., solid oral medications) to be dispensed to a patient 30. The medication dispensing device 20 may be located in the patient's home or other convenient location. The medication dispensing device may dispense one or more medications to the patient at various times according to prescribed schedules. The medication dispensing device 20 may communicate with the patient 30 via a user interface 22. The medication dispensing device 20 may also communicate with the patient 30 via other features (e.g., an alarm) and/or via a peripheral device 24 and/or a patient mobile device 32. In an aspect, a caregiver 70 or other party, such as a member of a care network, may interact with the medication dispensing device 20.

The peripheral device 24 may be any suitable device that may obtain medical or biometric data from a patient. For example, the peripheral device 24 may be a glucometer, cardiac monitor, thermometer, respiratory monitor, sleep monitor, pulse oximeter, body scale, inhaler, nebulizer, fitness tracker, blood pressure cuff, syringe, stethoscope, breathalyzer, mobile phone sensor, etc. The peripheral device 24 may provide measurements or biometric data to the medication dispensing device 20, for example, which may in turn transmit the measurements or biometric data to other devices via a network 40.

The medication dispensing device 20 may be communicatively coupled to a network 40. The network 40 may include any network that allows communication between the various entities of the system 10. In an aspect, the network 40 may be a communications network and may include or be connected with other networks. For example, the medication dispensing device 20 may include a modem and be coupled to the network 40 via a wired or wireless connection. The network 40 may include one or more computer servers 42. The computer servers 42 may include information for managing the medication dispensing device 20 and/or a peripheral device 24. In an aspect, for example, the computer servers 42 may include device servers for controlling one or more medication dispensing devices 20, notification servers for providing messages to the patient 30, caregivers 70, or others, such as the remote care team 80. The servers 42 may also receive data generated by medication dispensing device 20 and/or peripheral device 24. The computer servers 42 may also include one or more web servers running web applications that may allow a pharmacy 50, payer 60, caregivers 70, or others, such as the remote care team 80 to interact with the system 10 in defined roles. The computer servers 42 may also include storage servers for storing device information, medication information, patient information, billing information, etc.

In one aspect of the disclosure, various data is, for example, input and/or accessed by the patient 30, pharmacy 50, payer 60, caregivers 70, or other users via terminals such as personal computers (PCs), minicomputers, mainframe computers, microcomputers, telephonic devices, or wireless devices, personal digital assistants ("PDAs") or a hand-held wireless devices (e.g., wireless telephones). The terminals may be coupled to a computer server 42, such as a PC, minicomputer, mainframe computer, microcomputer, or other device having a processor and a repository for data and/or connection to a repository for data, via, for example, the network 40, such as the Internet or an intranet, and/or a wireless network. The couplings 44 include, for example, wired, wireless, or fiber optic links.

The medication dispensing device 20 may dispense medications provided by a pharmacy 50. In an aspect, a medication may include a solid oral medication (e.g., pills, caplets, capsules, gel caps, tablets, or tabs). In an aspect, the medication may include a prescription medication. The medication may also include over the counter medicine, vitamins, supplements, placebos, or other substances that may be dispensed to the patient 30. The pharmacy 50 may provide medications to the patient for storage in the medication dispensing device 20. The pharmacy 50 may receive prescription information from a doctor via written or electronic script, for example. The pharmacy 50 may fill the prescription and provide the medications to the patient 30 or caregiver 70 in a medication container, for example. The pharmacy 50 may submit medication information to the network 40 indicating the medication type, medication name, condition, total mass/weight, container mass/weight, mass/weight per unit of medication, and/or other medication properties for each medication.

In an aspect, the pharmacy 50 may provide a "quantity sufficient inventory." A quantity sufficient inventory may refer to an amount of medication to bring a patient's supply of the medication to a prescribed amount for a time period (e.g., an appropriate amount for proper ingestion in a 30 day period). The pharmacy 50 may receive current medication amounts from the medication dispensing device 20 via the network 40 to determine the quantity sufficient inventory. Among other things, providing a quantity sufficient inventory may reduce waste from missed doses and reduce medication costs.

The payer 60 may receive billing information from the network 40 and provide payment. For example, a server 42 may be a billing server that receives bills from the pharmacy 50 and provides the bills to the payer 60.

The remote care team 80 may receive information from the network 40 regarding a patient 30 and operations of the medication dispensing device 20. The remote care team, for example, may monitor for health changes and change prescription schedules.

Further details of the system 10 and its operation are provided in co-pending application No. 15/216,488, which is hereby incorporated by reference herein in its entirety for all purposes.

Figure 2A:
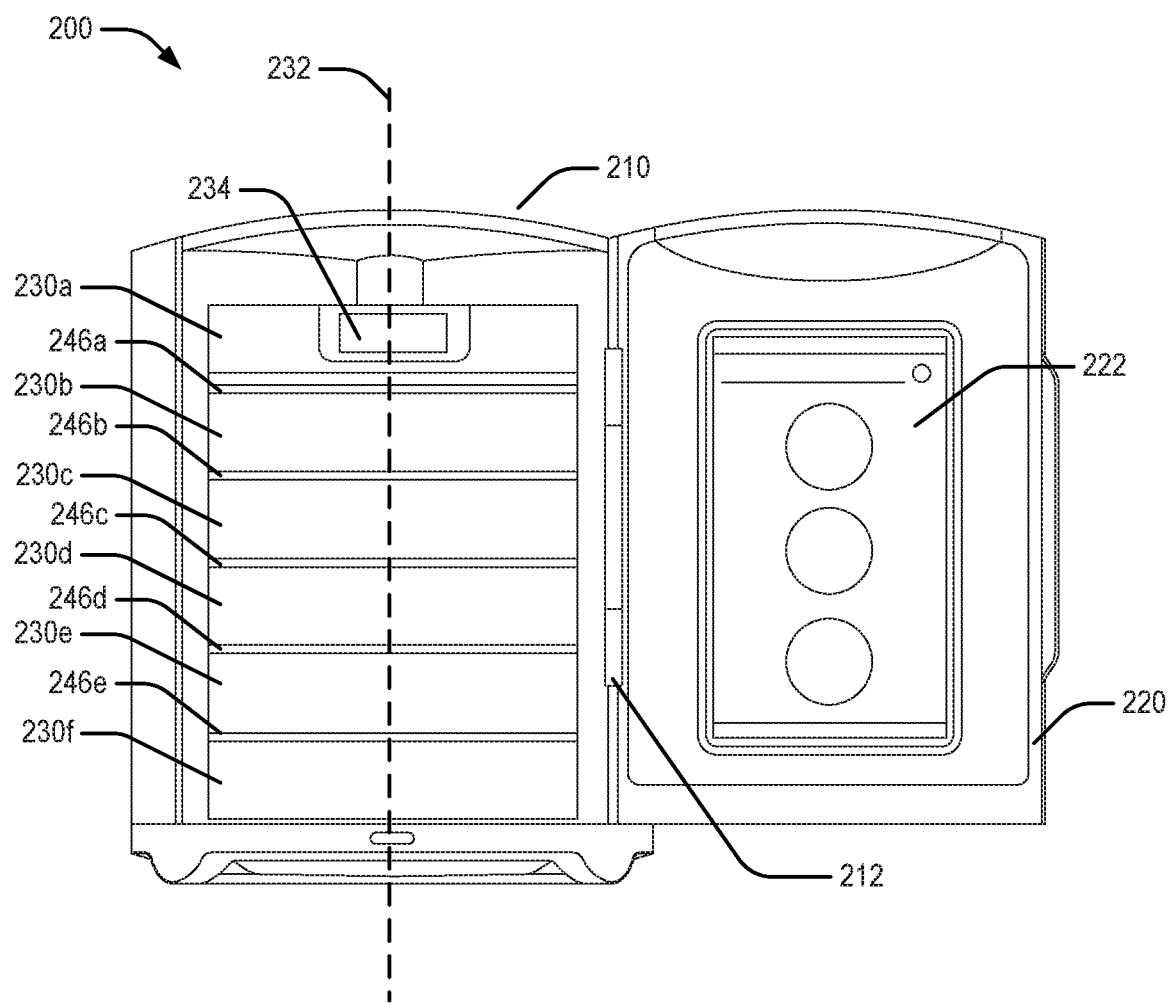
FIG. 2A-2E illustrate a front view in a medication accessible position, a front view in a medication inaccessible position, a front view in a closed position, a side view in a closed position, and a rear view in a closed position, respectively, of an example medication dispensing device in accordance with aspects of the present disclosure.

FIG. 2A illustrates a front view of an example medication dispensing device 200. The medication dispensing device 200 may be an example of the medication dispensing device 20 of FIG. 1. The medication dispensing device 200 may include a main body 210 and a door 220. The door 220 may be coupled to the main body 210 via a hinge 212 or other connecting mechanism. For example, the hinge 212 may be a double hinge allowing the door 220 to align flush with the main body 210. A double hinge may also protect wires communicatively coupling components of the door 220 with componennts of the main body 210. The door 220 may move between an open position (as illustrated in FIG. 2A) for use and a closed position (as illustrated in FIGS. 2C-2E) for travel or compact storage. In an aspect, the medication dispensing device 220 may include a sensor to determine a door status indicating whether the door 220 is, for example, fully closed, fully open, or partially open. For example, a Reed switch or proximity sensor may determine whether the door 220 is closed. The door status may control whether the medication dispensing device 220 moves a tray 230 to a medication dispensing position. The door status may also be used to activate the user interface 222.

In an aspect, the door 220 may include a user interface 222, which may correspond to the user interface 22 (FIG. 1). In other aspects, the user interface 222 may be located on the main body 210, on another portion of the medication dispensing device 200, or remote from the medication dispensing device 200. The user interface 222 may include, for example, a monitor, touch screen, keyboard, button, camera, microphone, speakers, mouse, stylus, and/or other input/output device or combination thereof. The user interface 222 may provide instructions to a patient 30 (FIG. 1) for operating the medication dispensing device 200. The user interface 222 may, for example, provide alerts and instruct the patient 30 to take a medication. The user interface 222 may also ask the patient 30 (FIG. 1) questions and receive answers. In an aspect, the user interface 222 may include additional lights (e.g., high powered LEDs) or a remote device to provide alerts to the patient. The user interface 222 may also provide service codes or other information. In an aspect, a service port (e.g., USB) may allow the medication dispensing device 200 to be connected with a diagnostic device.

The main body 210 may include multiple trays 230a-230f for storing and dispensing medication. The trays 230a-230f may be arranged vertically and/or horizontally. For example, the trays 230a-230f may be arranged along a vertical axis 232. In an aspect, the trays 230a-230f may be arranged in various manners, for example, with two or more trays in the same horizontal plane or "floor." The trays 230a-230f may, for example, be selectively placed in a medication accessible position, in which a patient may remove or otherwise access medication contained in a tray. For example, as illustrated in FIG. 2A, the tray 230a may be placed in a medication accessible position, such that the patient 30 (FIG. 1) may remove medication from an opening at the top of the tray 230a. The tray 230a may, for example, slide out of the main body 210 or rotate about a pivot point (e.g., a pin located at a corner of the tray 230a) so as to be partially out of the main body 210, such that the upper portion of the tray 230a may be accessible for removal of the medication. The tray 230a may include an indicia 234. The indicia 234 may identify the contents of the tray 230a and associated information such as patient information, refill information, prescribed mass/weight of medication, number of units of medication, mass/weight per unit of medication, dose size, expiration date, etc. In an aspect, the indicia 234 may be affixed to a medication container placed in the tray 230a. The indicia 234 may be machine readable, for example, in the form of a bar code, quick response (QR) code, machine readable text, magnetic stripe, radiofrequency (RF) tag, near field communication (NFC) tag, etc. In an aspect, the indicia 234 may include or be associated with an identifier of the medication, which may, for example, be linked to medication information provided by the network 40 (FIG. 1).

Figure 2B:
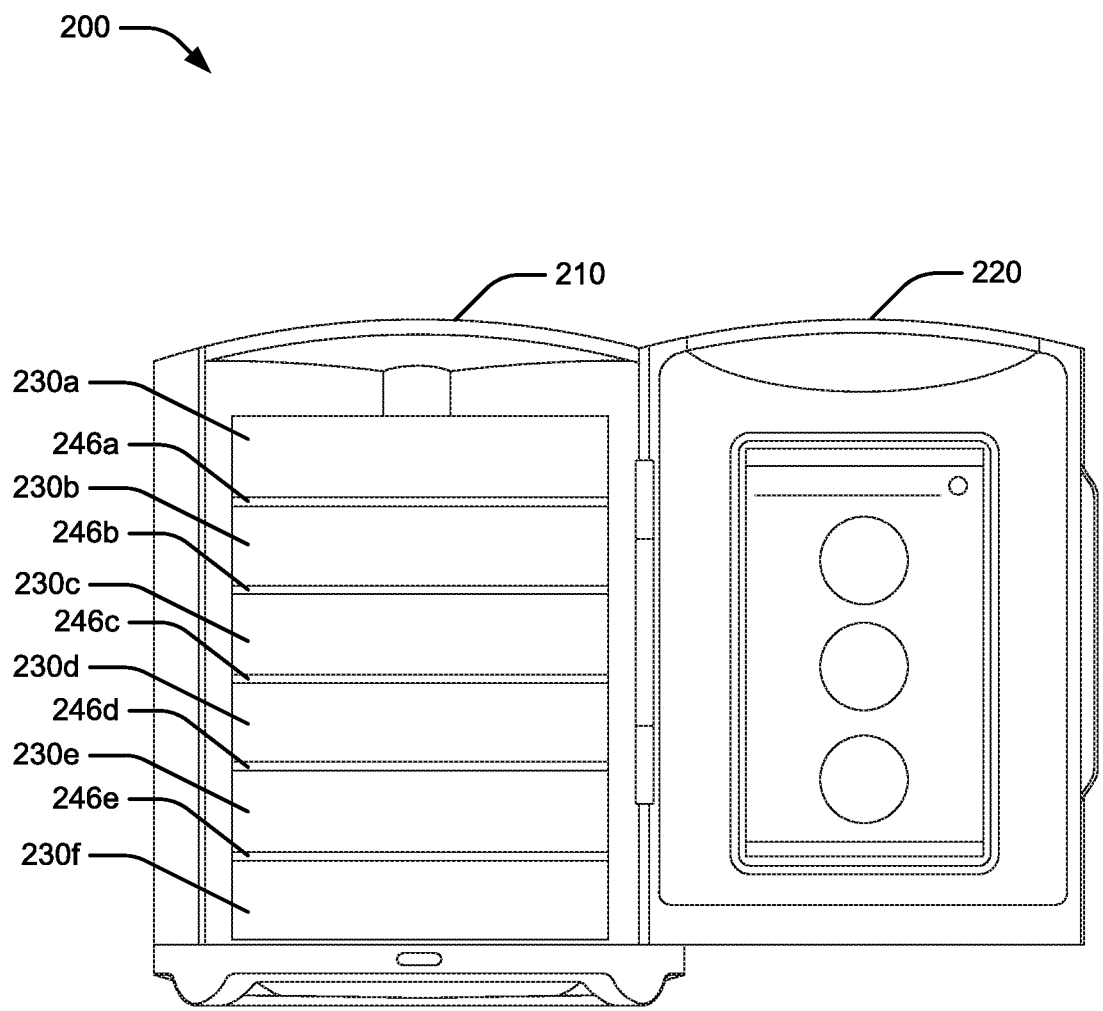
Figure 2C:
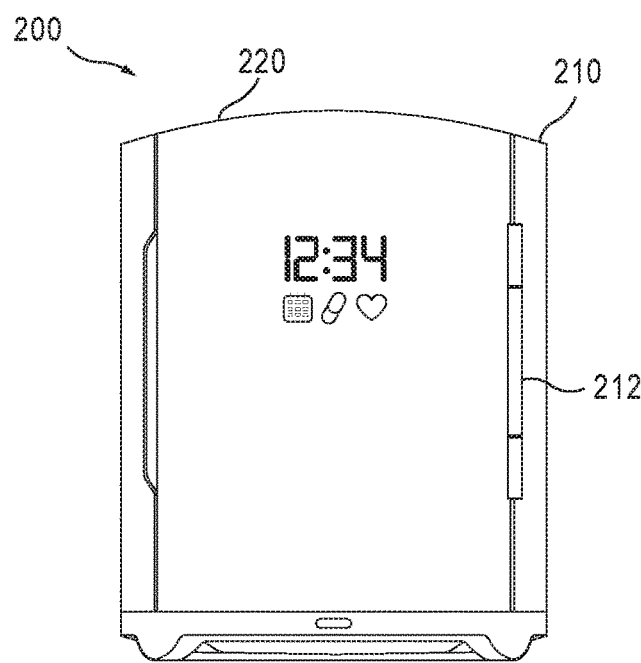
Figure 2D:
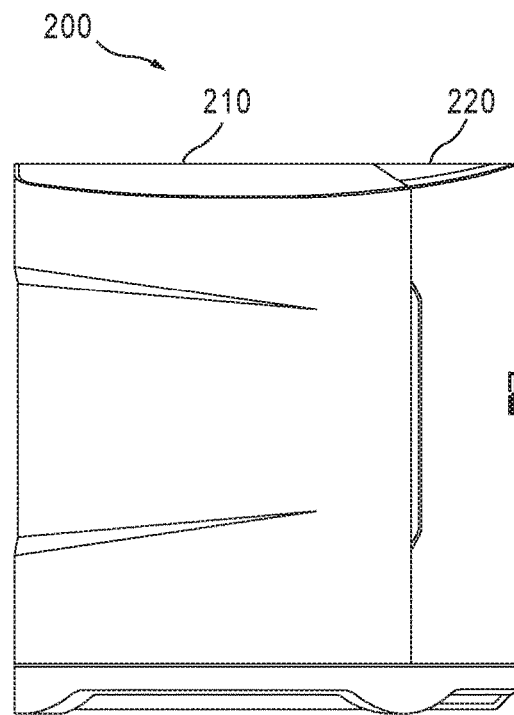
Figure 2E:
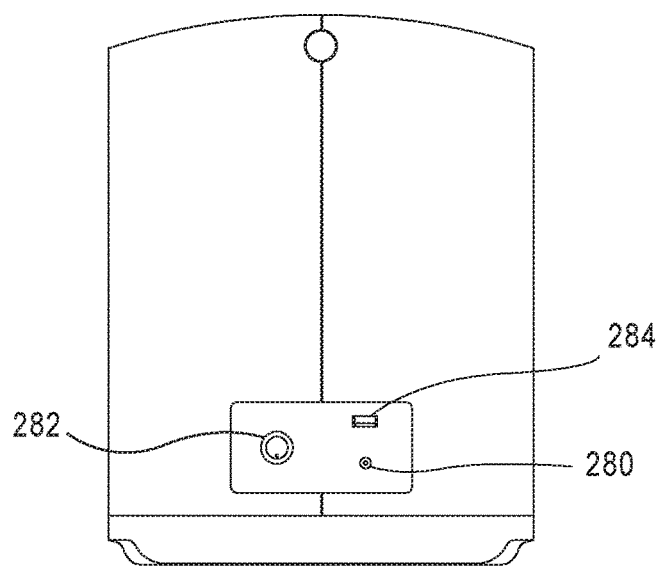
Figure 17:
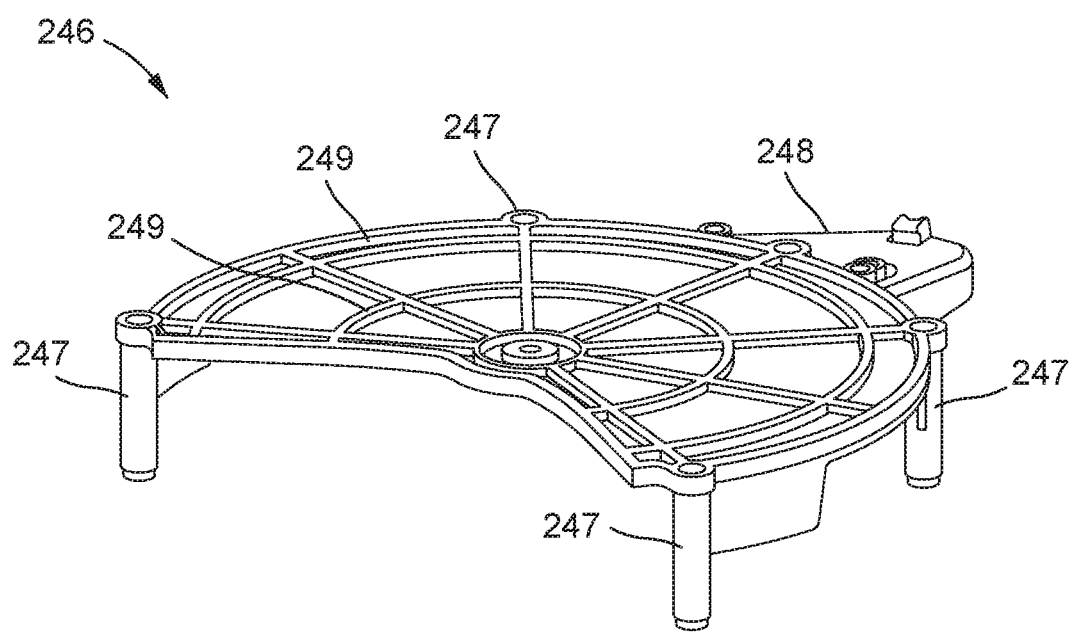
FIG. 17 illustrates an example of a tray divider in accordance with aspects of the present disclosure.

The trays 230a-230f (as illustrated in FIG. 2B) may each be placed in a medication inaccessible position. For example, each of the trays 230a-230f may be positioned such that an opening at the top of each tray 230a-230f is located within the inside the main body 210. Each tray 230a-230f may be selectively locked in such position, for example, such that the contents of each tray 230a-230f, when in this position, may not be accessed. In an aspect, the main body 210 may include tray dividers 246 positioned between trays. FIG. 17 illustrates further details of an example tray divider 246. The tray dividers 246 may allow the trays 230 to close with little clearance, effectively closing the tray 230 when the tray 230 is inside the main body 210. The clearance between the tray dividers 246 and the trays 230 may prevent the tray dividers from interfering with measurements by the load cells. In an aspect, the tray dividers 246 may be modular and provide spacing for a single tray 230 such that a tolerance for the clearance is not cumulative. For example, each tray divider 246 may have posts 247 that separate the tray divider 246 from an adjacent tray divider 246. The tray 230 may rest on top of a tray divider 246 and ride along one or more semi-circular ridges 249 on the tray divider 246 when rotating. The tray dividers 246 may be stacked and aligned using rods passing through the posts 247. Each tray divider 246 may further include a mounting portion 248 for mounting sensors and/or a driving mechanism for operating a respective tray 230.

The main body 210 may further include a power supply 280, a power switch 282, and a service port 284. The power supply 280 may accept a DC voltage and charge a battery. The power switch 282 may have an on position, an off position, and a low power position. The low power position may be selected for manual access. In an aspect, a service port 284 (e.g., USB) may allow the medication dispensing device 200 to be connected (e.g., via USB) with a diagnostic device.

Figure 3A:
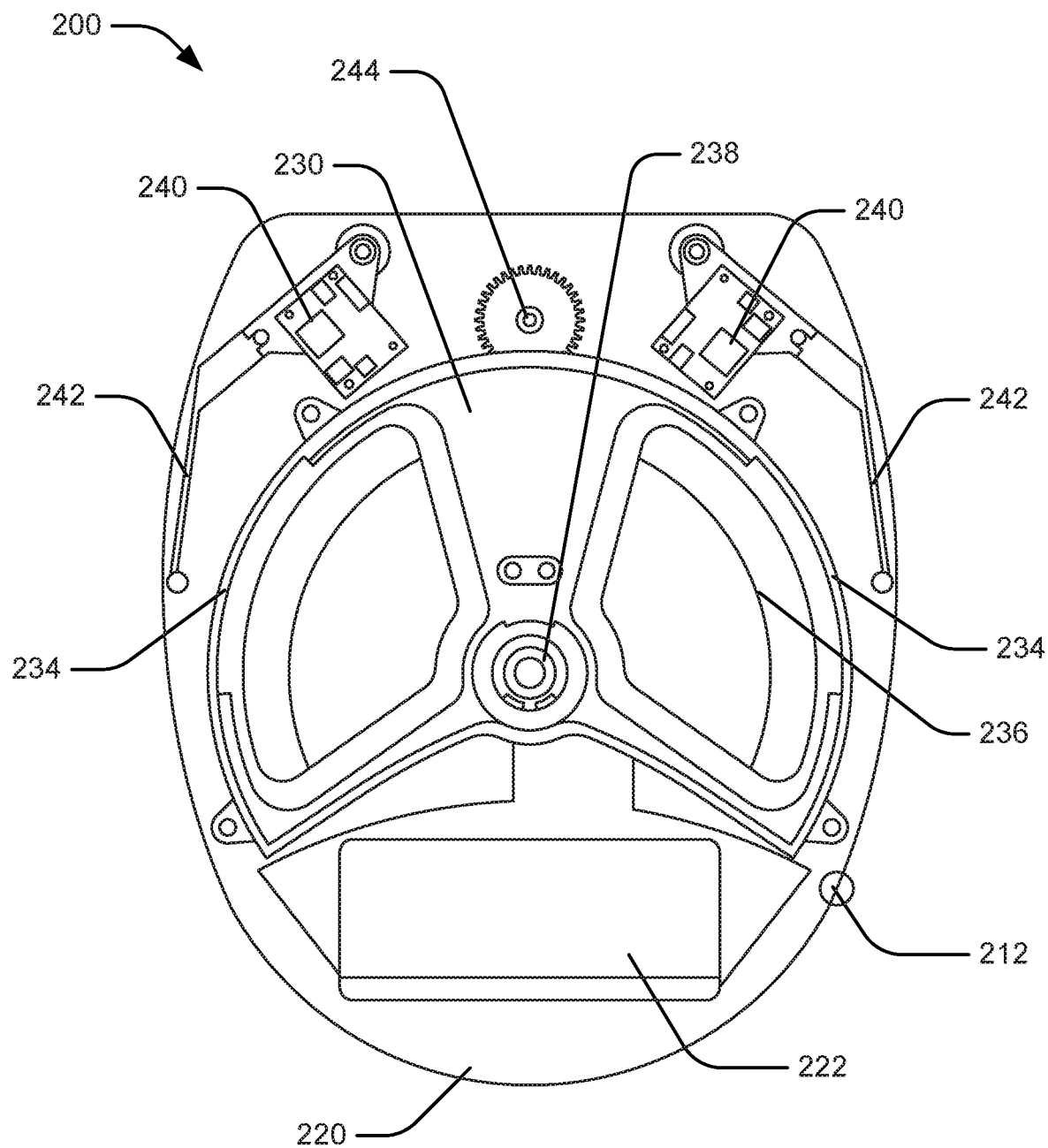
FIGS. 3A-3D illustrate a partial cutaway view of an example medication dispensing device in accordance with aspects of the present disclosure.

FIG. 3A illustrates a partial cutaway view of the example medication dispensing device 200. As illustrated in FIG. 3A, the door 220 of the medication dispensing device 200 is in a closed position. As illustrated in FIG. 3, the medication dispensing device 200 may include one or more scanners 240, which may include hardware and/or software, for reading the indicia 234. For example, the scanners 240 may include bar code scanners, QR scanners, RF readers, NFC devices, etc. In an aspect, the medication dispensing device 200 may include one or more mirrors 242 or other reflective surfaces for assisting the scanners 240 with reading the indicia 234. The mirrors 242 may be, for example, front-face mirrors. Use of such mirrors 242 may, for example, allow for flexibility in the position of the scanners 240 and thus enable a more compact design.

In an aspect, the scanners 240 and mirrors 242 may be integrated into a scanning unit. The scanning unit may be mounted, for example, on lead screws or threaded rods to allow the scanning unit to move vertically. The lead screws may be driven by a motor via a timing belt such that the scanning unit moves along all of the lead screws uniformly. The motor may move the scanning unit to an approximate position of a tray 230 and the scanners 240 may scan multiple times while moving. In an aspect, the scanning unit may traverse the height of the medication dispensing device 200 in approximately 6 seconds. Accordingly, a single scanning unit may be used to scan different trays 230a-230f (FIG. 2A).

A tray 230 may include one or more medication containers 236. A medication container may also be referred to as a pod or RxPod. In an aspect, a medication container 236 may be removable from the tray 230. For example, the medication container 236 may rest in a container port of the tray 230. The indicia 234 may, for example, be located on a tab that overhangs the tray 230 or may be readable by another feature, such as an opening in a portion of the tray 230. A second indicia may be located on the tray 230 behind the indicia 234 and be readable only when no medication container 236 is in the container port. The second indicia may indicate that the container port is empty. In another aspect, the medication container 236 may be integrally formed with the tray 230, or medication may be placed in a container port. A support feature 238, such as a vertical rod, may be located, for example, at or parallel to the vertical axis 232 (FIG. 2) and may extend through the main body 210. The trays 230 may be mounted to and rotate about the support feature 238. In an aspect, a driving mechanism 244, such as an electric motor, a solenoid, or a biasing (e.g., spring) based mechanism, may be used to selectively move the trays 230. For example, the driving mechanism 244 may be coupled to a gear, pulley, or other mechanical device that selectively rotates each of the trays 230 between a medication accessible position and a medication inaccessible position. The driving mechanism 244 may be controlled by a controller, which may include, for example, a processor, which may optionally be integrated with features relating to the user interface 222, for example.

Figure 3B:
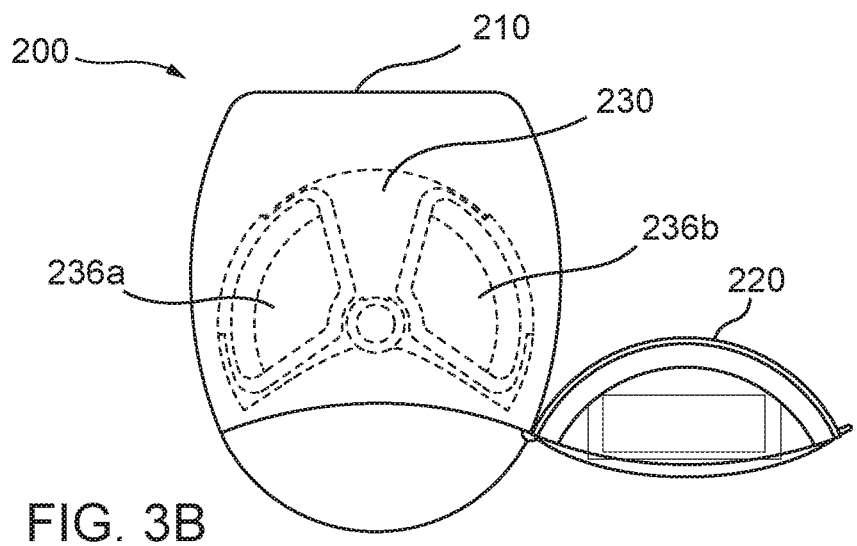
Figure 3C:
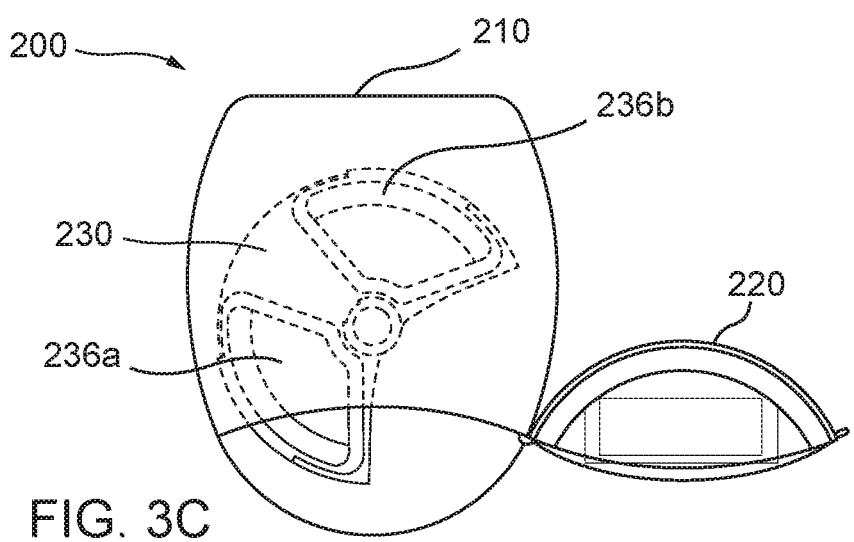
Figure 3D:
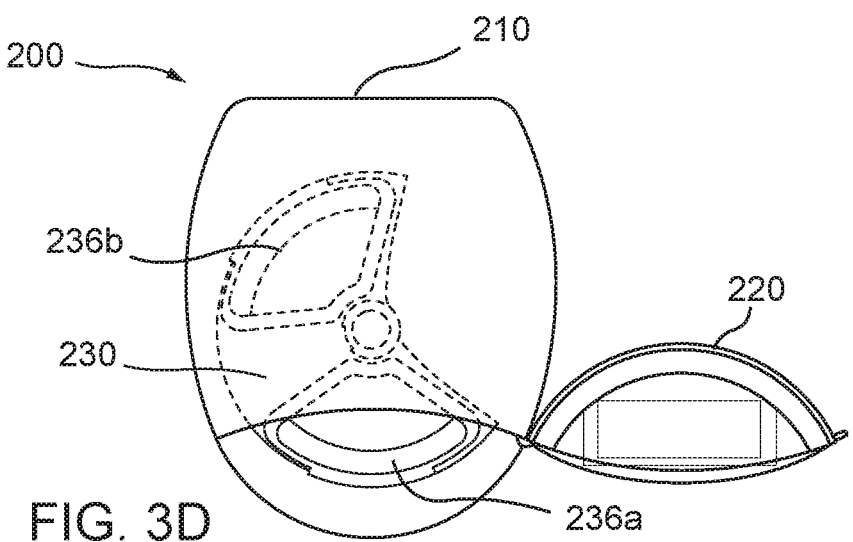

FIG. 3B illustrates the example medication dispensing device 200 with the door 220 in an open position and the tray 230 in a medication inaccessible position. The tray 230 may include two medication containers 236a and 236b, which may both be located within the main portion 210 and covered by a tray divider 246 (not shown). FIG. 3C illustrates the example medication dispensing device 200 with the door 220 in an open position and the tray 230 in a partially medication accessible position. For example, the medication container 236a may be partially exposed in the partially medication accessible position. FIG. 3D illustrates the example medication dispensing device 200 with the door 220 in an open position and the tray 230 in a medication accessible position. The medication container 236a may be completely exposed in the medication accessible position. In an aspect, the driving mechanism 244 may rotate the tray 230 counterclockwise from the position shown in FIG. 3B through the position shown in FIG. 3C to the position shown in FIG. 3D. The driving mechanism 244 may also rotate the tray 230 in the opposite direction to return the tray 230 to the medication inaccessible position. In an aspect, the driving mechanism may rotate the tray 230 in a clockwise direction to reach a medication accessible position in which the medication container 236b is exposed.

In an aspect, the driving mechanism 244 may include a manual access feature that allows access when the medication dispensing device 200 does not have external power. For example, the manual access feature may include a cam shaft that may be rotated to decouple gears of the driving mechanism 244. When the cam shaft is rotated to a manual access position, the separation of the gears may allow each of the trays 230 to be manually rotated to a medication accessible position. In an aspect, the manual access feature may also activate the power switch 282 to indicate whether the manual access feature was activated. The power switch 282 may be connected to the cam shaft and switch to lower power mode when the cam shaft is rotated. The switch 282 may place the medication dispensing device 200 in a low power mode to conserve battery power. The switch 282 may also initiate a calibration sequence upon repowering of the medication dispensing device 200 to detect the position of each of the trays 230 and place the trays 230 in the medication inaccessible position. The calibration sequence may also include displaying user instructions on the user interface 222 and/or determining current amounts of medication.

Figure 4:
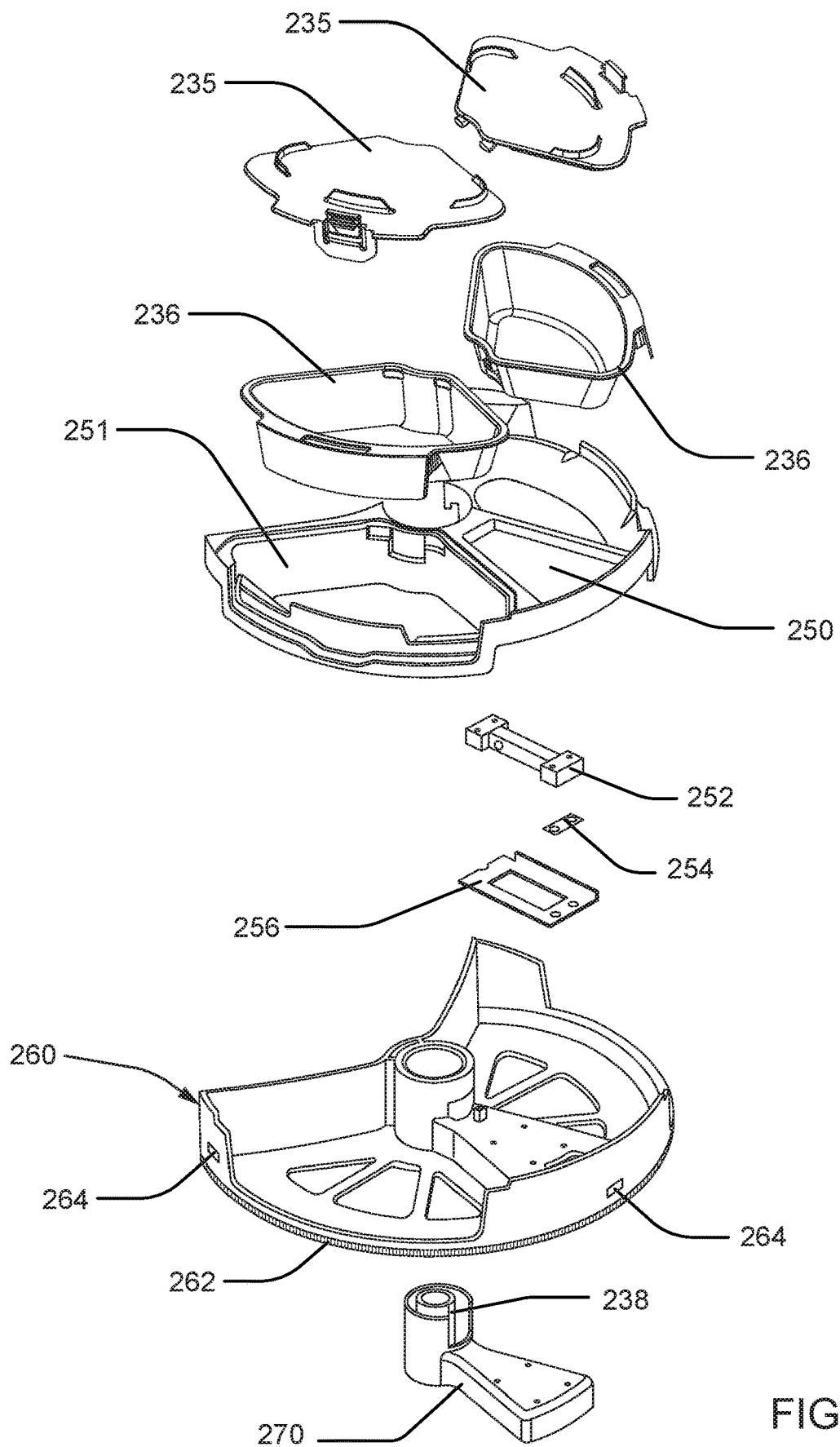
FIG. 4 illustrates an exploded view of an example tray in accordance with aspects of the present disclosure.

FIG. 4 illustrates an exploded view of an example tray 230 (e.g., corresponding to trays 230a-230f of FIG. 2A). The tray 230 may include features to retain one or more medication containers 236 via a container holder 250, and a structural support portion 260. The container holder 250 may include one or more container ports 251 for receivably retaining the medication containers 236. In an aspect, the medication containers 236 may rest in or otherwise be retained by the container ports 251. In another aspect, the medication containers 236 may releasably engage the container ports 251. The structural support portion 260 may be mounted to or otherwise interact with or operate relative to the support feature 238. The structural support portion 260 may include a rack of teeth 262 or other similar features for engaging a gear to rotate the tray 230. The structural support portion 260 may support a load cell 252 between the structural support portion 260 and the container holder 250. The load cell 252 may measure a weight or mass. The load cell 252 may also be interchangeably referred to herein as a strain gauge, scale, etc. The load cell 252 may provide a measurement to a processor. The load cell 252 may be mounted between the structural support portion 260 and container holder 250, such as by a bracket 256 and clip 25, and/or other appropriate hardware or other features. Accordingly, the load cell 252 may be configured to measure the mass/weight of the container holder 250 and any inserted medication containers 236, including medication therein. In an aspect, the load cell 252 may be configured with a tare feature to remove the weight of the container holder 250 and/or empty medication containers 236.

In an aspect, a press switch may be used to detect the rotational position of a tray 230. For example, a tray 230 may include notches 264 at various positions. The press switch may generate a signal when aligned with a notch 264, allowing the processor or controller to detect the rotational position of the tray 230. The processor or controller may control the driving mechanism 244 based on the press switch to align the trays 230 in a medication inaccessible position. The processor or controller may control the driving mechanism 244 based on the press switch to stop rotation of a tray 230 upon reaching a medication accessible position.

The support bracket 270 may position the structural support portion 260 on the support feature 238. The support bracket 270 may provide load bearing strength for supporting the support portion 260. For example, the support bracket 270 may be formed from a stronger material (e.g, glass filed nylon) than the material (e.g., plastic) of the support portion 260. The load cell 252 may also be mounted to the support bracket 270. The support bracket 270 may include circuitry and wiring for the load cell 252. For example, the support bracket 270 may include an amplifier for amplifying the signal from the load cell 252 for transmission to the processor. The support bracket 270 may include one or more openings for wires or cables to pass from the load cell 252 into an area adjacent the support feature 238. The wires may pass vertically adjacent to the support feature 238 between vertically adjacent support brackets 270 to the top or bottom of the medication dispensing device 200 (FIG. 2A).

Figure 5A:
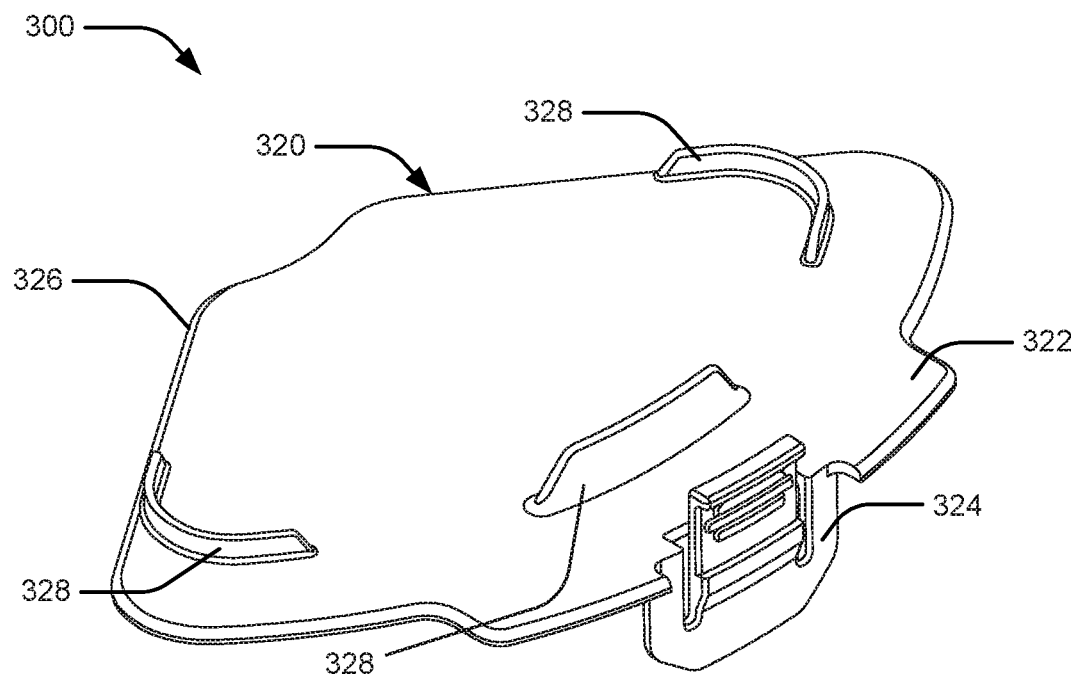
FIGS. 5A and 5B illustrate exploded perspective and side views, respectively, of an example medication container in accordance with aspects of the present disclosure.
Figure 5A:
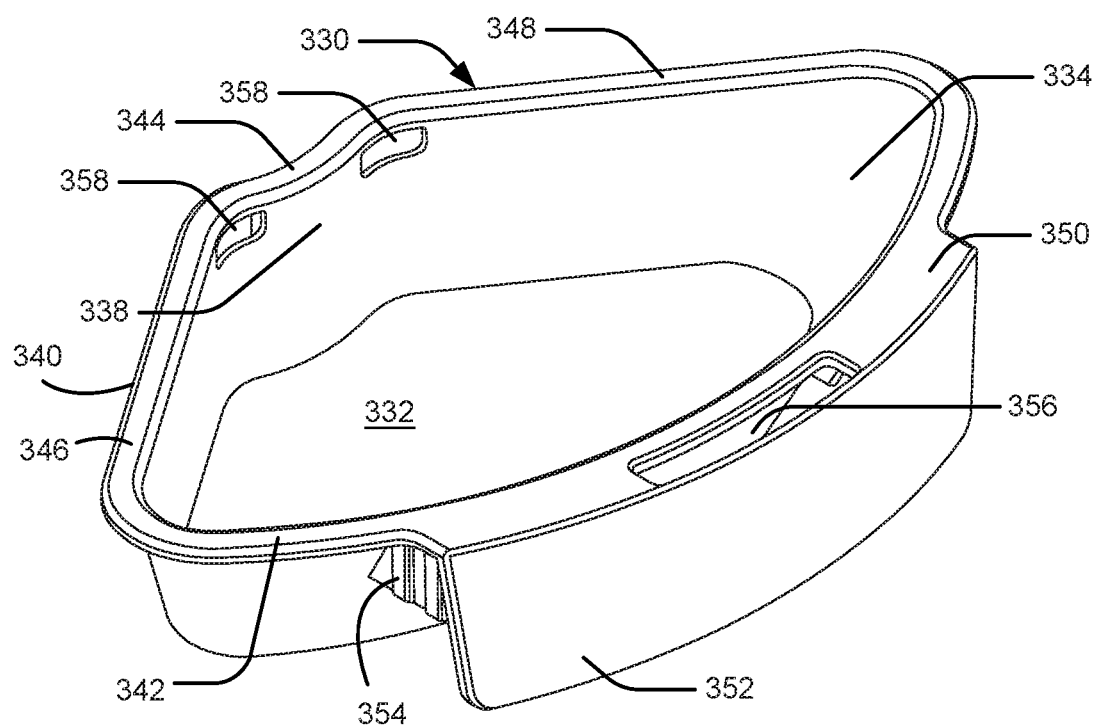
Figure 5B:
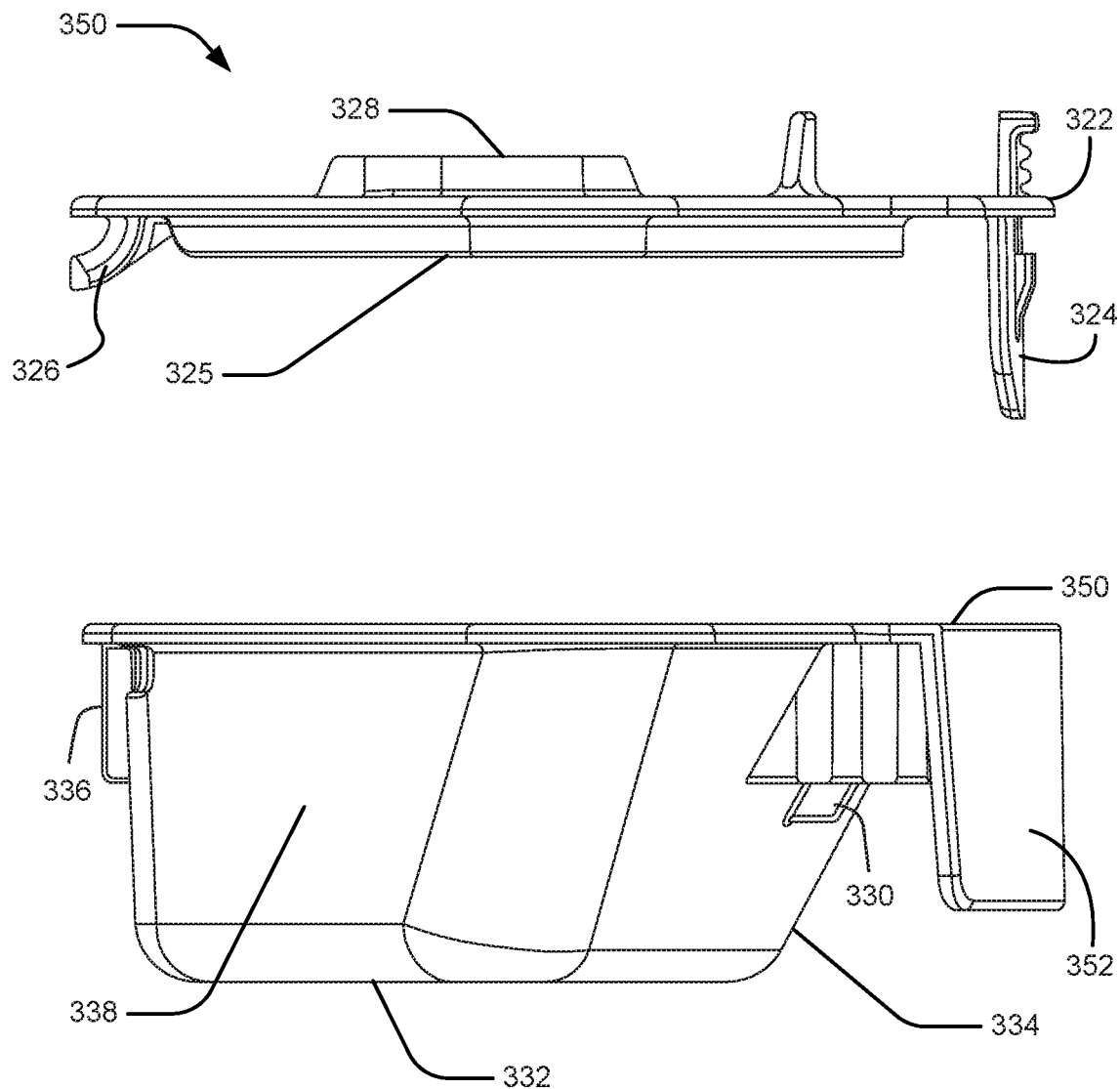

FIG. 5A illustrates an exploded perspective view of an example medication container 300. FIG. 5B illustrates an exploded side view of the example medication container 300. The medication container 300 may be an example of, or include, a medication container 236, as shown in FIG. 4, and may be used with a medication dispensing device 200 as shown in FIGS. 2 and 3. The bowl 330 may store medication. The bowl 330 may be shaped to fit in a medication dispensing device (e.g., medication dispensing device 200) and allow easy removal of medication. In one example implementation, the bowl 330 may have a top edge 340. The top edge 340 may include a convex arc segment 342, a concave arc segment 344, and straight connecting segments 346, 348 that connect the ends of the arc segments 342, 344. In one example implementation, the convex arc segment 342 and concave arc segment 344 may be concentric. For example, when placed in a tray 230, the convex arc segment 342 and concave arc segment 344 may be centered at the vertical axis 232 and/or rotate about the support feature 238. The bowl 330 may include a generally flat bottom surface 332, for example, that may allow the bowl 330 to securely rest on a flat surface, such as a table or scale. The bowl 330 may also include a sloped or curved bottom surface 334 or portion thereof. The bottom surface 334 may have an angle of approximately 45°-70° from horizontal, preferably approximately 62°. In an aspect, the 330 may have generally vertical or steep side walls 338 between the flat bottom surface 332 and the concave arc segment 344 and the straight connecting segments 346, 348. The sloped or curved bottom surface 334 may extend from the flat bottom surface 332 toward the convex arc segment 342. In an aspect, the shape of the medication container 300 or bowl 330 may allow easy removal of medication. The convex arc segment 342 may face a user when the medication container 300 is placed in the medication dispensing device 200, for example. The long convex arc segment 342 may allow the user to easily insert a portion or all of a hand into the medication container 300. For example, the long convex arc segment may have a length in the range of 2 to 8 inches, preferably approximately 4-6 inches. The short concave arc segment 344 may have a length in the range of ½ to 2 inches, preferably around 1 inch. The distance between the long convex arc segment and the short concave arc segment may be in the range of 2 inches to 4 inches, preferably in the range of 2.5 inches to 3.5 inches. The sloped or curved bottom surface 334 may allow the user to slide a medication up to the convex arc segment 342 and out of the medication container 300. For example, a single pill may be removed without needing to pinch the pill between two fingers, although such pinching motion may also be used to remove medication from the medication container 300. The sloped or curved bottom surface 334 may be an uninterrupted surface to allow easy sliding. Further, the transition between the flat bottom surface 332 and the sloped or curved bottom surface may have a radius of at least 5 millimeters to prevent medication from catching on the transition. In an aspect, the bowl 330 may have a volume sufficient to hold at least 30 units of any human ingestible solid oral medication.

The bowl 330 may further include a handle 350 extending from the top edge 340 along the convex arc segment 242. For example, the handle 350 may be centered on the convex arc segment 242. The handle 350 may include a vertical surface 352 that may be generally parallel to the convex arc segment 342. The vertical surface 352 may bear an indicia 234. The handle 350 may also include a support feature 354 to strengthen the handle 350. For example, the support feature 354 may be corrugated. The handle 350 may also include a front locking feature 356. For example the front locking feature 356 may be a slot for receiving a tab. The bowl 330 may include one or more rear locking features 358 located in the vertical wall 338 between the bottom surface 332 and the concave arc segment 344 of the top outer edge 340. For example, the rear locking features 358 may be a pair of slots. Each slot may be smaller than a unit of solid oral medication (e.g., a pill).

The lid 320 may be removably attached to the bowl 330. The lid 320 may generally have a shape matching the top edge 340. The lid 320 may have lip 325 matching at least a portion of an internal or external surface of the top edge 340 of the bowl 330. The lip 325 may prevent medication from being removed while the lid 320 is attached to the bowl 330. In an aspect, the lip 325 may form a press fit or interference fit with the bowl 330.

A tab 322 may extend from a convex arc portion of the lid 320 corresponding to the handle 350. The tab 322 may extend further than the handle 350 and/or be narrower than the handle 350. The handle 350 may include a textured surface for gripping while manipulating the lid 320. The tab 322 may also include a vertical locking tab 324 that engages the front locking feature 356. For example, the vertical locking tab 324 may include a flexible portion having a shoulder that engages the front locking feature 356. In an aspect, the flexible portion may be hinged at a bottom of the vertical locking tab 324 and extend to a handle portion above the shoulder. The handle portion may be textured to provide a place to grip. The lid 320 may include one or more rear tabs 326 that engage the rear locking features 358. For example, the rear tabs 326 may be hooks that curve downwardly from the lid 320.

In an aspect, the lid 320 may be positioned on the bowl 330 by inserting the rear tabs 326 into the rear locking features 358 and pivoting the lid 320 down onto the top edge 340. The vertical locking tab 324 may flex as it is inserted through the front locking feature 356 until the shoulder moves past a ridge of the vertical surface 352. The vertical locking tab 324 may then releasably engage the ridge of the vertical surface 352. The lid may be removed by pressing on the handle portion of the vertical locking tab 324 and lifting tab 322. The handle portion may be pinched toward a center stacking feature 328. In an aspect, the lid 320 may be removed from the bowl 330 while the medication container 300 is within a container port 251 (FIG. 4). In an aspect, a user may lift on the tab 322 while holding the handle 350 to remove the lid 320. In an aspect, the medication container 300 may allow removal of the lid 320 without placing excessive force on a load cell 252.

As illustrated in FIG. 5B, the medication container 300 may include features for stacking multiple medication containers 300. The lid 320 may include ridges 328 that may correspond to the edges of the bottom surface 332 of the bowl 330. The bottom surface 332 may fit within the ridges 328 such that a medication container 300 may be stacked on top of the lid 320 of a closed medication container 300. The bowl 330 may also include a front stacking feature 335 and a rear stacking feature 336. The front stacking feature 335 may be a standing rib that may space a top bowl from a curved or sloped surface 334 of a bottom bowl. The rear stacking feature 336 may include one or more vertical standing ribs. A bottom of the rear stacking feature 336 may provide a ledge that rests on the top edge 340 of the bottom bowl. The support feature 354 may also rest on the top edge 340 of the bottom bowl. Accordingly, the bowls 330 may be stacked without lids allowing for a reduction in total volume. Moreover, the rear stacking feature 336 may also engage a corresponding feature of the container port 251 (FIG. 4)

Figure 6:
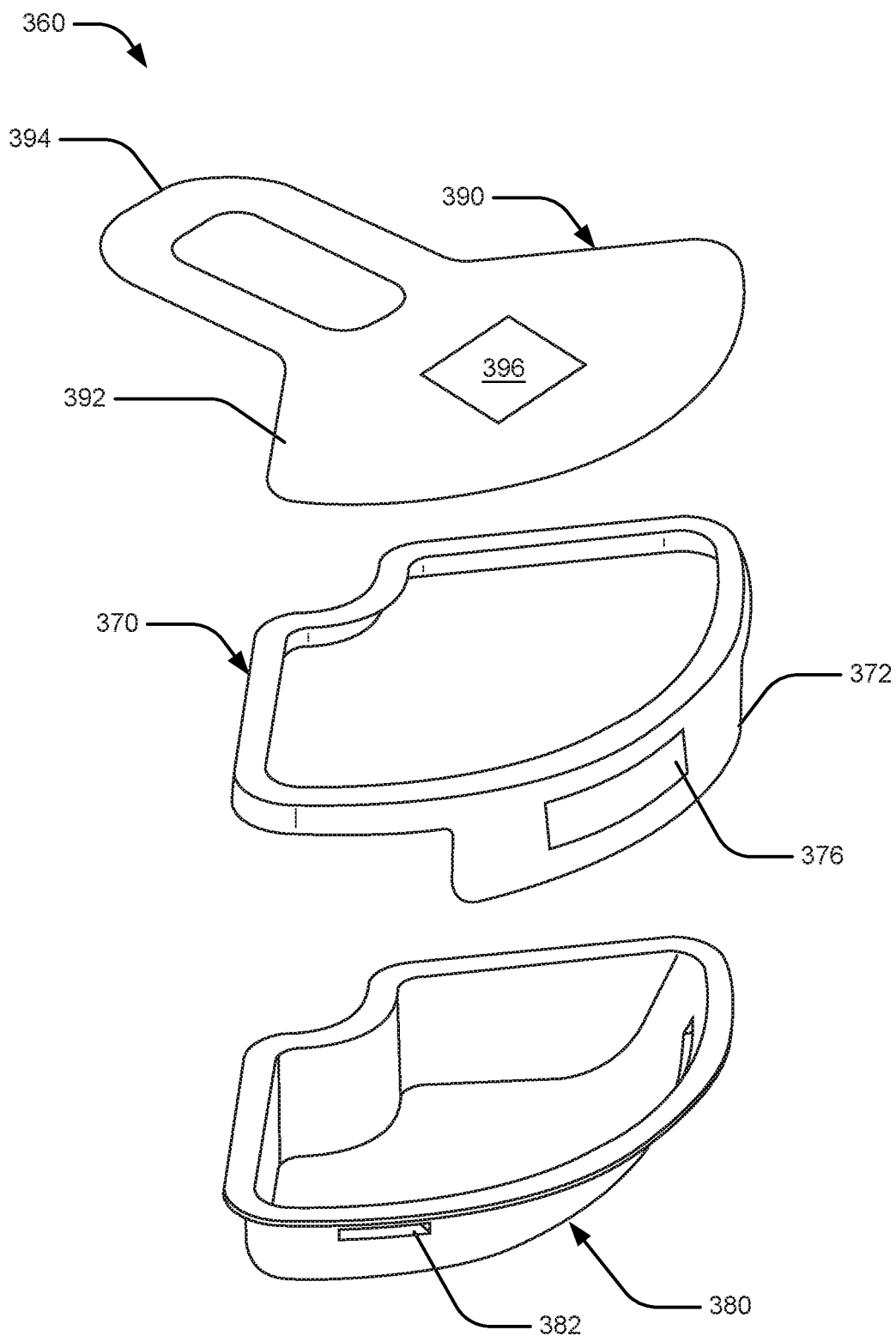
FIG. 6 illustrates an exploded view of another example medication container in accordance with aspects of the present disclosure.

FIG. 6 illustrates an exploded view of another example medication container 360. The medication container 360 may include a lid 370, a bowl 380, and a seal 390. The bowl 380 may have a similar general shape as the bowl 330 (FIGS. 5A and 5B). The medication container 350 may include a lid 370, and a bowl 380. In one example implementation, the medication container 350 may be provided to a pharmacy, for example, with the seal 390 detachably attached to the lid 370. For example, the seal 390 may be adhered to the lid 370. The pharmacist may place within the medication container 350 a prescribed medication and seal the medication container 350 by placing the lid 320 on the bowl 330.

The lid 370 may be removably attached to the bowl 380. The lid 370 may have an internal surface matching the top outer edge 340 of the bowl 380, such that the lid 370 may form a press fit or interference fit with the bowl 380. One or more locking features 382 may secure the lid 370 to the bowl 380. The locking features 382 may optionally form a child-resistant closure of the medication container 360. A tab 372 may be also be located on the lid 370, such as extending downwardly from a convex segment of the lid 370. The tab 372 may be concentric with the convex arc segment 342 and include an indicia 376, for example, which may enable more accurate scanning as the medication container 300 rotates along with a tray 230.

The seal 390 may seal the medication container 360 for transport. The seal 390 may be removable by a user (e.g., a caregiver or patient) before or after insertion into a medication dispensing device (e.g., medication dispensing device 200). In an aspect, the seal 390 may comprise a foil that is adhered to the lid 370. The seal 390 may include a main body portion 392 that is sized and shaped to match the lid 370. The main body portion 392 of the seal 390 may also include a label including indicia 396, which may be similar to the indicia 234. The seal 390 may also include a handle portion 394 that may extend beyond an edge of the lid 370. The handle portion 394 may thereby allow a user (e.g., a patient) to easily grasp the seal 390 for removal, for example.

Figure 7:
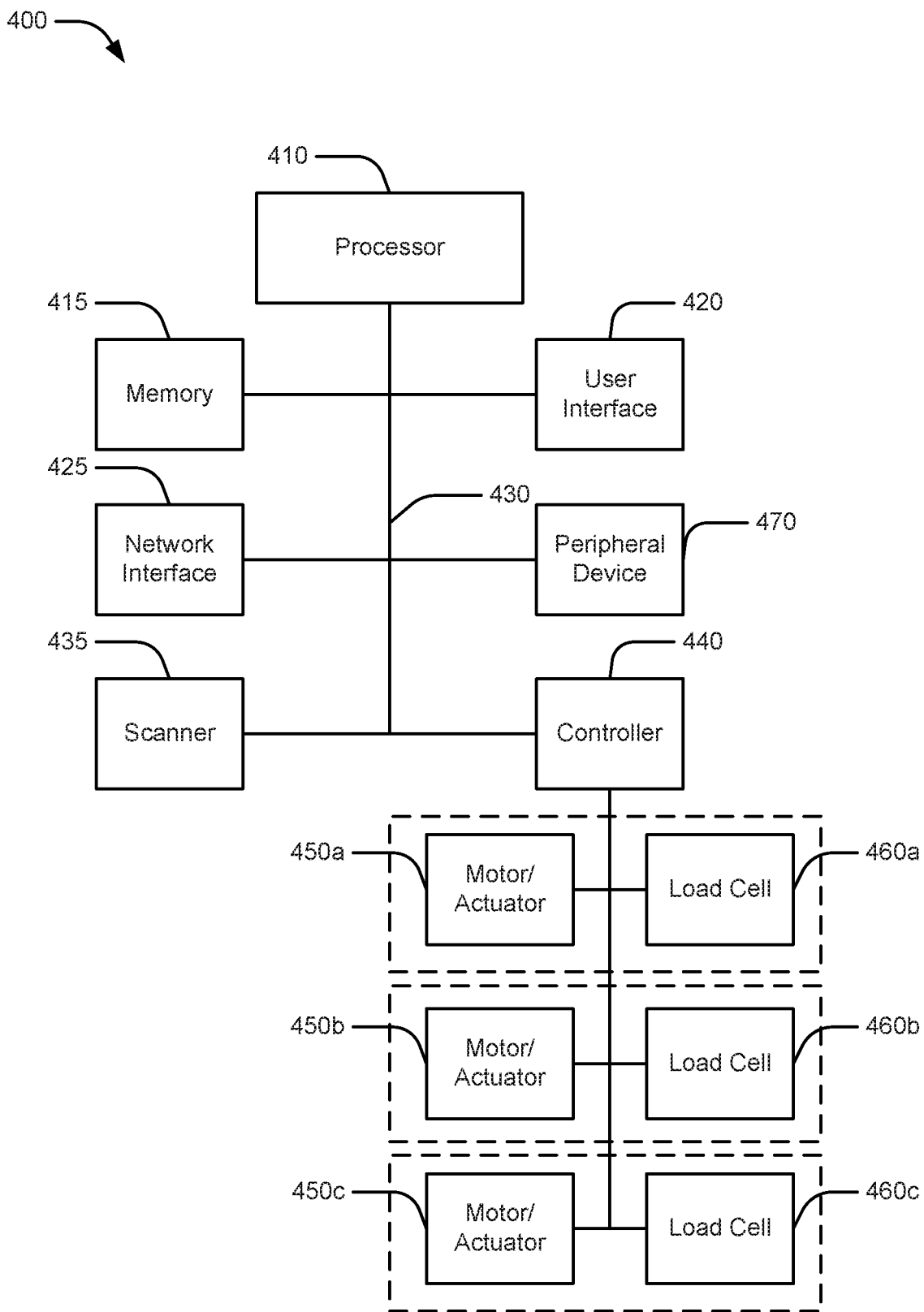
FIG. 7 contains a representative block diagram illustrating various aspects of an example control system for a medication dispensing device in accordance with aspects of the present disclosure.

FIG. 7 contains a representative block diagram illustrating various features of an example control system 400 for a medication dispensing device. The control system 400 may include a processor 410, memory 415, user interface 420, network interface 425, bus 430, scanner 435, and controller 440. The control system 400 may also include electronic components of the dispensing device, such as motor/actuators 450a-n and load cells 460a-n, where n may correspond to a number of trays in the medication dispensing device. In an aspect, one or more scanners 435 may also be associated with each tray.

The processor 410 may be a general purpose computer processor capable of executing instructions. For example, the processor 410 may execute software instructions stored in memory 415. The software instructions, when executed by the processor 410, may cause the processor 410 to control the other components of the control system 400 via the bus 430, as described herein. The memory 415 may store instructions executable by the processor 410. In an aspect, the memory 415 may be considered a computer-readable medium. The memory 415 may also store information or data that is manipulated by the processor 410. For example, the memory 415 may store patient information, medication information, etc.

The user interface 420 may correspond to the user interface 22 or user interface 222. In an aspect, the user interface 420 may also correspond to a mobile device of the user (e.g., patient mobile device 32 (FIG. 1)). The user interface 420 may output images and/or sounds to a user, such output including, for example, instructions, menus, questions, pictures, videos, etc. The user interface 420 may receive user input such as answers, selections, etc. (e.g., via voice input device, or keyboard, button(s), mouse, mobile device, or other similarly functioning input mechanism).

The network interface 425 may provide an interface between the control system 400 and the network 40. In an aspect, for example, the network interface 425 may include a modem for communication via a wired or wireless connection to the network 40.

The bus 430 may connect the other components of the control system 400. The bus 430 may be controlled by the processor 410, for example, to transfer instructions (e.g., movement instructions) and/or data among components.

The scanner 435 may correspond to the scanner 240 (FIG. 3). The scanner 435 may read an indicia 234 on a tray 230 or a medication container 236 and provide information to the processor 410. For example, the scanner 435 may be used to obtain or determine information corresponding to the indicia 234 (FIG. 3).

The controller 440 may control one or more motor/actuators 450 and/or load cells 460. For example, the controller 440 may receive instructions from the processor 410 to place a tray in a medication accessible position or a medication inaccessible position (e.g., a position in which a user may access medication within the tray, or a position where a user may not so access medication). The controller 440 may identify/enable a motor/actuator indicated for use by the instructions and control the identified/enabled motor/actuator so as to cause movement of the appropriate tray. For example, the controller 440 may determine a direction of turning for a motor and energize the motor until a selected tray moved by the motor reaches a desired position. As another example, the controller 440 may energize an actuator (e.g., solenoid) to lock or unlock a door or move a tray. Further, the controller 440 may enable operation of and/or receive information from the load cells 460. For example, the controller 440 may power on a load cell 460 to obtain a measurement of mass/weight for a tray. The controller 440 may also provide a received measurement from a designated load cell to the processor 410, the memory, or another device/system.

The peripheral device 470 may correspond to the peripheral device 24 (FIG. 1). The peripheral device 470 may be connected to the control system 400 via, for example, a wired (e.g., universal serial bus (USB) connection or a wireless (e.g., Bluetooth) connection. The peripheral device 470 may provide measurements, biometric data, user input, or other information to the processor 410, for example, which may in turn transmit the information to other devices via the network interface 425 and network 40. The processor 410 may further send and receive data via the user interface 420 relating to providing instructions for using the peripheral device 470, for example.

Figure 8:
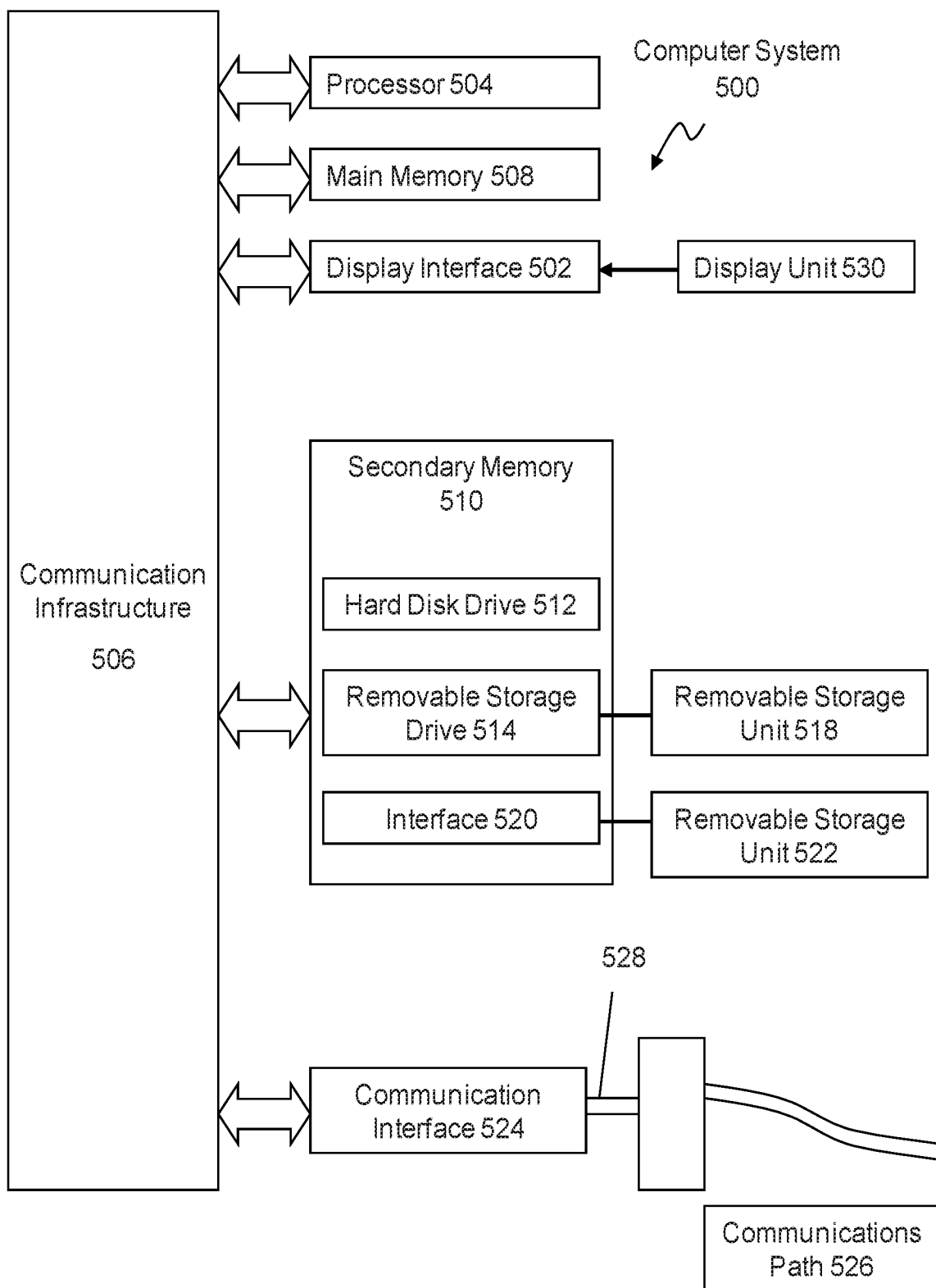
FIG. 8 contains a representative block diagram illustrating various aspects of an example computer system in accordance with aspects of the present disclosure.
Figure 9:
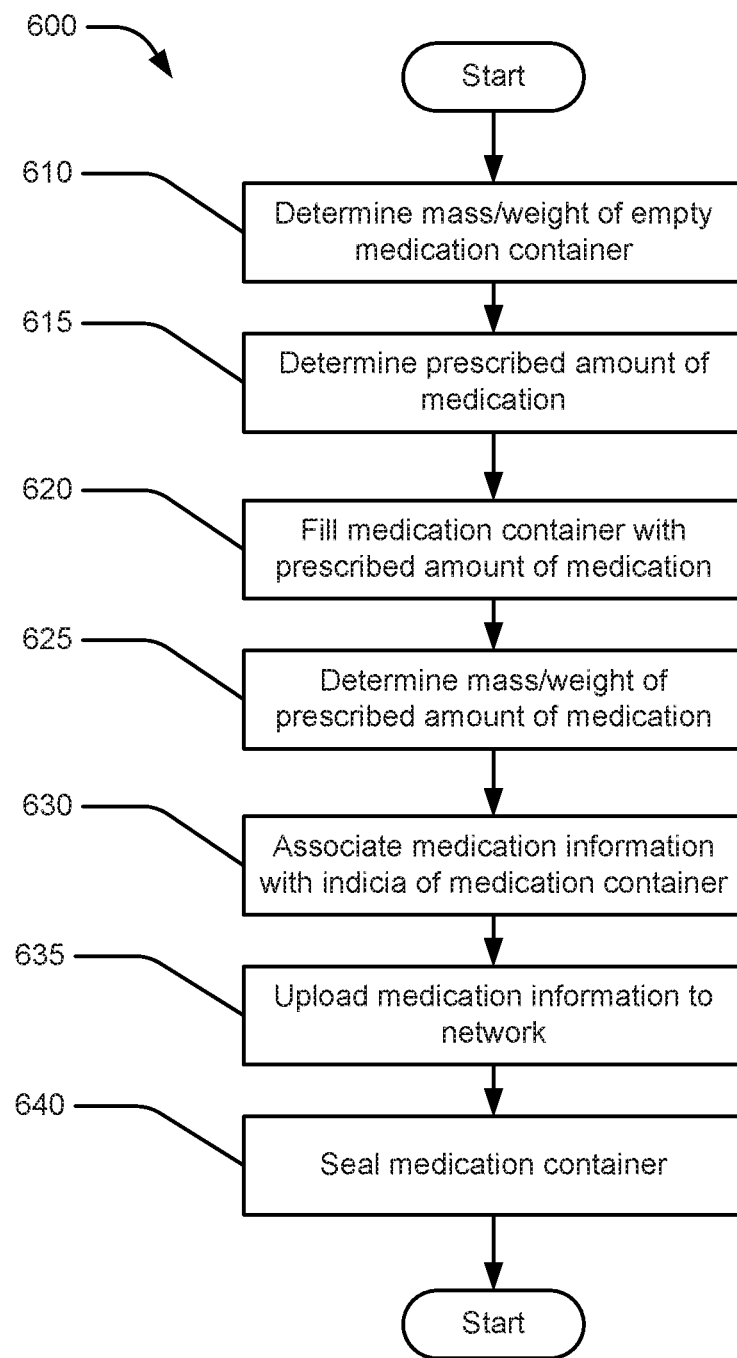
FIG. 9 is a flowchart illustrating an example method of filling a medication container.

Aspects of the present invention may be implemented using hardware, software, or a combination thereof and may be implemented in one or more computer systems or other processing systems. For example, the user interface 222 (FIG. 2) may be implemented as a computer system or processing system. Also, the control system 400 (FIG. 7) may be implemented as a computer system or processing system. In an aspect of the present invention, features are directed toward one or more computer systems capable of carrying out the functionality described herein. An example of such a computer system 500 is shown in FIG. 8.

Computer system 500 includes one or more processors, such as processor 504. The processor 504 is coupled to a communication infrastructure 506 (e.g., a communications bus, cross-over bar, or network). Various software aspects are described in terms of this example computer system. After reading this description, it will become apparent to a person skilled in the relevant art(s) how to implement aspects hereof using other computer systems and/or architectures.

Computer system 500 may include a display interface 502 that forwards graphics, text, and other data from the communication infrastructure 506 (or from a frame buffer not shown) for display on a display unit 530. Computer system 500 may include a main memory 508, preferably random access memory (RAM), and may also include a secondary memory 510. The secondary memory 510 may include, for example, a hard disk drive 512 and/or a removable storage drive 514, e.g., an optical disk drive. The removable storage drive 514 may read from and/or write to a removable storage unit 518 in a well-known manner. As will be appreciated, the removable storage unit 518 may include a computer readable storage medium having stored therein computer software and/or data.

Alternative aspects of the present invention may include secondary memory 510 and may include other similar devices for allowing computer programs or other instructions to be loaded into computer system 500. Such devices may include, for example, a removable storage unit 522 and an interface 520. Examples of such may include a program cartridge and cartridge interface (such as that found in video game devices), a removable memory chip (such as an erasable programmable read only memory (EPROM), or programmable read only memory (PROM)) and associated socket, and other removable storage units 522 and interfaces 520, which allow software and data to be transferred from the removable storage unit 522 to computer system 500.

Computer system 500 may also include a communications interface 524. Communications interface 524 may allow software and data to be transferred among computer system 500 and external devices. Examples of the noted communications interface 524 may may include a modem, a network interface (such as an Ethernet card), a communications port, a Personal Computer Memory Card International Association (PCMCIA) slot and card, etc. Software and data transferred via communications interface 524 may be in the form of signals 528, which may be electronic, electromagnetic, optical or other signals capable of being received by communications interface 524. These signals 528 may be provided to communications interface 524 via a communications path (e.g., channel) 526. This path 526 may carry signals 528 and may be implemented using wire or cable, fiber optics, a telephone line, a cellular link, a radio frequency (RF) link and/or other communications channels. As used herein, the terms "computer program medium" and "computer usable medium" refer generally to media such as a removable storage drive 580, a hard disk installed in hard disk drive 570, and/or signals 528. These computer program products may provide software to the computer system 500. Aspects of the present invention are directed to such computer program products.

Computer programs (also referred to as computer control logic) may be stored in main memory 508 and/or secondary memory 510. Computer programs may also be received via communications interface 524. Such computer programs, when executed, may enable the computer system 500 to perform the features in accordance with aspects of the present invention, as discussed herein. In particular, the computer programs, when executed, may enable the processor 504 to perform the features in accordance with aspects of the present invention. Accordingly, such computer programs may represent controllers of the computer system 500.

Where aspects of the present invention may be implemented using software, the software may be stored in a computer program product and loaded into computer system 500 using removable storage drive 514, hard disk drive 512, or interface 520. The control logic (software), when executed by the processor 504, may cause the processor 504 to perform the functions described herein. In another aspect of the present invention, the system may be implemented primarily in hardware using, for example, hardware components, such as application specific integrated circuits (ASICs). Implementation of the hardware state machine so as to perform the functions described herein will be apparent to persons skilled in the relevant art(s).

In yet another variation, aspects of the present disclosure may be implemented using a combination of both hardware and software.

FIG. 8 is a flowchart illustrating an example method 600 of filling a medication container such as medication container 300 or medication container 350. In an aspect, the method 600 and related methods may be performed by a pharmacy 50 (FIG. 1) using a pharmacy scale and/or a pharmacy computer terminal. As used herein, the term "pharmacy" may be used to refer to a pharmacist, technician, or any other employee of a pharmacy or pharmacist. In another aspect, the method 600 may be performed by a patient 30 or caregiver 70. For example, the patient 30 or caregiver 70 may use the medication dispensing device 20 (FIG. 1) or a peripheral scale. While, for purposes of simplicity of explanation, the methods are shown and described as a series of steps or acts, it is to be understood and appreciated that the methodologies are not limited by the order of acts, as some acts/steps may, in accordance with one or more aspects, occur in different orders and/or concurrently with other acts/steps from that shown and described herein. For example, it is to be appreciated that a methodology could alternatively be represented as a series of interrelated states or events, such as in a state diagram. Moreover, not all illustrated acts/steps may be required to implement a method in accordance with one or more aspects.

In block 610, the method 600 may include determining a mass/weight of an empty medication container. The pharmacy 50 may, for example, weigh an empty medication container. The pharmacy 50 may also determine the mass/weight based on an indication from the manufacturer. A patient 30 or caregiver 70 may similarly determine the mass/weight of an empty medication container.

At block 615, the pharmacy 50 may determine a prescribed amount of medication. In an aspect, the prescribed amount of medication may be an amount indicated on a prescription from a physician. In another aspect, the prescribed amount of medication may be a "quantity sufficient inventory" for a designated time period (e.g. 1 month). For a patient, the prescribed amount of medication may be indicated within prescription information provided by a pharmacist. As another example, a non-prescription medication may have an amount of medication indicated by a physician, nutritionist, or other health professional (e.g., one pill per day).

In block 620, the method 600 may include filling the medication container with the prescribed amount of medication. For example, the pharmacy 50 may count a number of units of medication or determine a mass/weight/volume of the medication when filling the medication container. A patient or caregiver may similarly count a number of units of medication.

In block 625, the method 600 may include determining a mass/weight of the prescribed amount of medication within the medication container. For example, the pharmacy 50 may subtract the mass/weight of the empty container from a mass/weight of the filled container. Similarly, a patient 30 or caregiver 70 may determine the mass/weight of the medication within the medication container. In an aspect, the medication dispensing device may be configured to provide instructions and/or automatically determine a mass/weight of medication within the medication container.

In block 630, the method 600 may include associating medication information with indicia of the medication information. The medication information may include prescription information, a mass/weight of the medication, a number of units of medication, a per unit mass/weight of the medication, the identifier of the indicia, and/or patient information. In an aspect, the per unit mass/weight of the medication may be supplied by a manufacturer and entered by the pharmacy 50. In another aspect, the pharmacy 50 may determine the per unit mass/weight of the medication based on the prescribed amount of medication and the mass/weight of the prescribed amount of medication. In an aspect, for example, a pharmacy label including an indicia may be applied to the medication container. In another aspect, the medication container may include a predetermined indicia and the pharmacy 50 may scan the indicia and associate an identifier of the indicia with both the medication container and the medication information.

In block 635, the method 600 may include uploading medication information to the network 40. In an aspect, for example, the pharmacy 50 may upload medication information to the network 40. The medication information may include prescription information, the mass/weight of the medication, the number of units of medication, the per unit mass/weight of the medication, the identifier of the indicia, and/or patient information. The network 40 may forward the medication information to the medication dispensing device 20. For a patient 30 or caregiver 70 the medication dispensing device 20 may upload the medication information to the network 40.

In block 640, the method 600 may optionally include sealing the medication container. For example, the pharmacy 50 may close the medication container and engage any locking features. The pharmacy 50 may provide the sealed medication container to the patient 30 or caregiver 70. In an aspect, a patient 30 or caregiver 70 may place the medication container into the medication dispensing device 20 without sealing the container.

Figure 10:
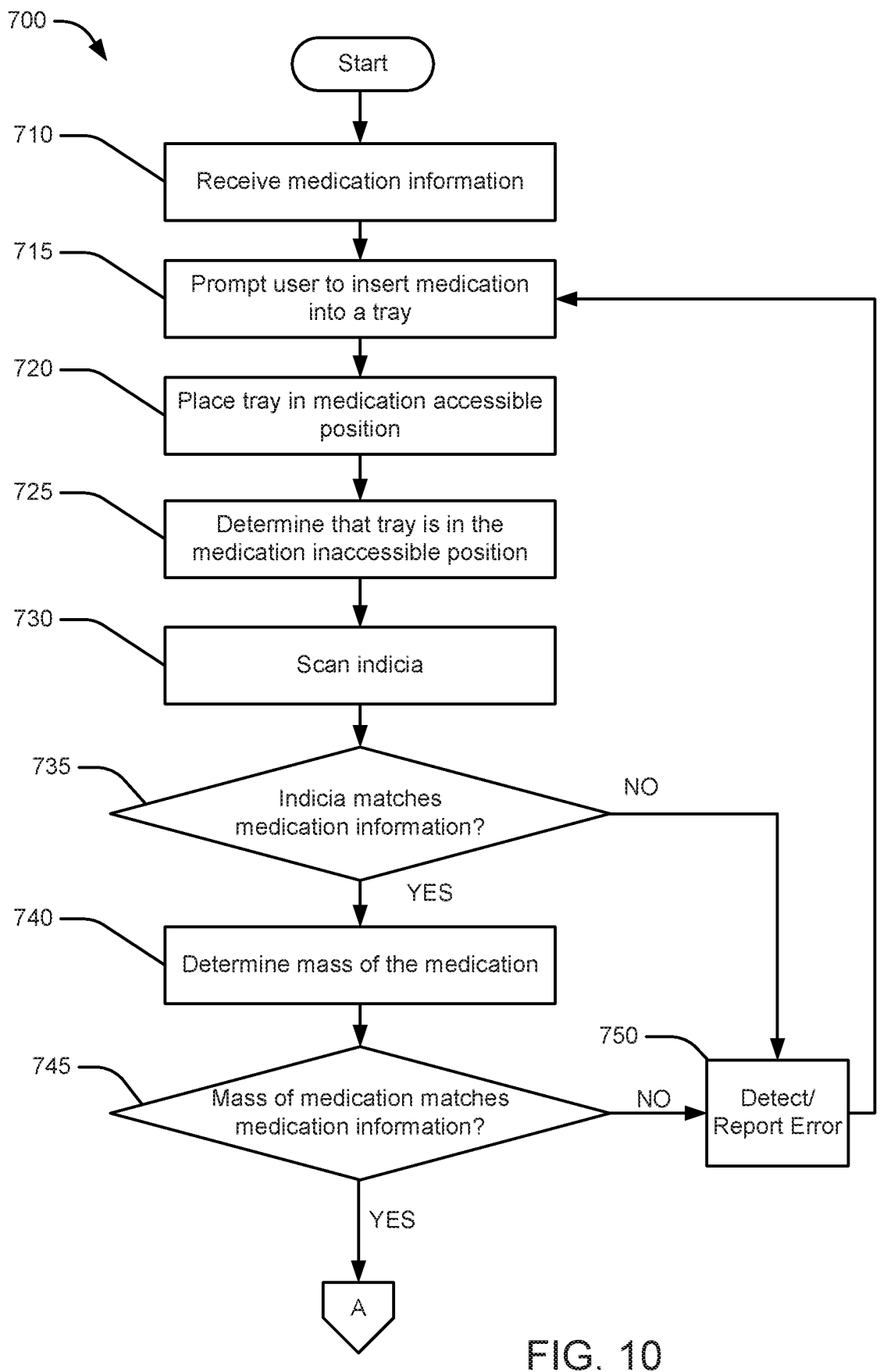
FIG. 10 is a flowchart illustrating an example method of loading a medication into a medication dispensing device in accordance with aspects of the present disclosure.

FIG. 10 is a flowchart illustrating an example method 700 of loading a medication dispensing device 20 (FIG. 1). In an aspect, the method 700 and related methods may be performed by a medication dispensing device 20 or medication dispensing device 200 (FIGS. 2 and 3). While, for purposes of simplicity of explanation, the methods are shown and described as a series of steps or acts, it is to be understood and appreciated that the methodologies are not limited by the order of acts, as some acts/steps may, in accordance with one or more aspects, occur in different orders and/or concurrently with other acts/steps from that shown and described herein. For example, it is to be appreciated that a methodology could alternatively be represented as a series of interrelated states or events, such as in a state diagram. Moreover, not all illustrated acts/steps may be required to implement a method in accordance with one or more aspects.

In block 710, the method 700 may include receiving medication information for medication to be dispensed from the medication dispensing device 20 (FIG. 1). The medication information may include, for example, a medication identifier, the prescribed medication mass/weight, the number of units of medication, the per unit mass/weight, and/or other properties of a medication. The medication information may be received, for example, via a network interface from the pharmacy 50 (FIG. 1) or other source via the network 40 (FIG. 1) or by direct input to the medication dispensing device 20 (FIG. 1), among other inputs. The received medication information may be stored in association with a tray 230 and/or a container port 251.

In block 715, the method 700 may include prompting for insertion of medication into a tray 230 (FIG. 2). In an aspect, for example, the user interface 22 (FIG. 1) or user interface 222 (FIGS. 2 and 3) may prompt for insertion of medication into a tray 230. In an aspect, for example, the user interface 22 (FIG. 1) may prompt for insertion of medication in response to receiving medication information. For example, the user interface may display a message identifying the medication to be inserted. In another aspect, a user may navigate a menu, press a button, scan an indicia, or otherwise provide input indicating that medication is to be inserted.

In block 720, the method 700 may include placing a tray in a medication accessible position. In an aspect, for example, the processor 410 may instruct controller 440 (FIG. 7) to place an identified tray in a medication accessible condition. For example, the processor 410 (FIG. 7) may select a tray associated with the medication to be made accessible. In an aspect, the processor 410 may associate the medication with an unassigned tray and instruct the controller 440 to place the unassigned tray in a medication accessible condition. The user interface user interface 22 (FIG. 1) or user interface 222 (FIGS. 2 and 3) may instruct the user to insert the medication into the tray.

Referring back to FIG. 10, in block 725, the method 700 may include determining that the tray is in the medication inaccessible position. In an aspect, for example, the controller 440 (FIG. 7) may indicate to the processor 410 (FIG. 7) that a tray is in the medication inaccessible position. Block 725 may also include controlling the tray to move the tray into the medication inaccessible condition, for example, by controlling a motor/actuator 450 (FIG. 7) in response to an indication received via the user interface 420 (FIG. 7) that the medication has been inserted. In an aspect where the scanner 435 (FIG. 7) is located internally to a medication dispensing device 200 (FIGS. 2, 3), the scanner 435 may detect that a tray is in a medication inaccessible condition by scanning an indicia 234 (FIGS. 2, 3) or by another position determining feature.

In block 730, the method 700 may include scanning an indicia. In an aspect, for example, the scanner 240 (FIG. 3) or scanner 435 (FIG. 7) may scan an indicia 234 (FIGS. 2, 3) or indicia 316 (FIG. 5). In an aspect where the scanner is located in the interior of the medication dispensing device, for example, scanning the indicia may further indicate that the tray is in a medication inaccessible condition. In an aspect where the scanner is located external to the medication dispensing device, the block 730 may be performed prior to the block 715, for example.

In block 735, the method 700 may include determining whether the scanned indicia matches received medication information. In an aspect, for example, the processor 410 (FIG. 7) may determine whether the scanned indicia matches the received medication information. For example, the processor 410 (FIG. 7) may compare a medication identifier included in the medication information with a medication identifier obtained by the scanner 435 (FIG. 7). If the indicia does not match the medication information, the method 700 may proceed to block 750. Otherwise, the method 700 may proceed to block 740.

In block 740, the method 700 may include determining a mass or weight of the medication. In an aspect, for example the processor 410 (FIG. 7) may determine the mass/weight of the medication based on a reading from a corresponding load cell 460 (FIG. 7). For example, the processor 410 (FIG. 7) may receive a reading from the corresponding load cell 460 (FIG. 7) that includes a mass/weight of the tray and/or a medication container. The processor 410 may subtract a known mass/weight of the tray and/or medication container or a previously measured mass/weight, for example, to determine the mass/weight of the medication. In another aspect, the load cell 460 (FIG. 7) may be configured to provide only the mass/weight of the medication. In an aspect, the processor 410 may determine a per unit mass/weight of the medication based on a number of medication units and the measured mass/weight of the loaded medication.

In block 745, the method 700 may include determining whether the mass/weight of the loaded medication matches the medication information. In an aspect, for example, the processor 410 (FIG. 7) may determine whether the mass/weight of the medication substantially matches the medication information. For example, the processor 410 (FIG. 7) may compare a prescribed mass/weight of medication in the received medication information with the measured mass/weight of medication. The processor 410 may allow a range of acceptable mass/weight or use a variation threshold to account for the accuracy of the load cell 252 and variation in the per unit mass/weight of medication units. If the mass/weight of medication does not substantially match the medication information, the method 700 may proceed to block 750. If the mass/weight of medication matches the medication information, the processor 410 may determine that the medication was inserted into the medication dispensing device correctly. The processor 410 may also store the final medication information in association with the tray. For example, the processor 410 may update a per unit mass/weight if the measured mass/weight varies slightly from a received mass/weight. The method 700 may then end, repeat for another medication to be loaded into the device 20, or continue to, for example, method 700, which is described in further detail below.

In block 750, the method 700 may include detecting, reporting, and/or correcting errors. In an aspect, for example, the processor 410 may determine that an error has occurred because the medication information does not match the inserted medication. The processor 410 (FIG. 7) may report the error to the network 40 (FIG. 1), for example, via the network interface 425 (FIG. 7). For example, reporting the error to the network 40 (FIG. 1) may facilitate referral to technical assistance or placement of a service call. Further, the processor 410 (FIG. 1) may attempt to correct/further determine the nature of the error. In an aspect, the processor 410 (FIG. 1) may instruct a patient or other user to take remedial or other action. For example, the processor 410 (FIG. 1) may control the user interface 420 (FIG. 1) to display an image of the medication and ask the user or other user to confirm that the medication in the tray matches the image. As another example, the processor 410 (FIG. 7) may control the user interface 420 (FIG. 7) to provide instructions to count the number of pills in the tray. The processor 410 (FIG. 7) may also return to block 715 and prompt for insertion of the same or a different medication into the tray.

Figure 11:
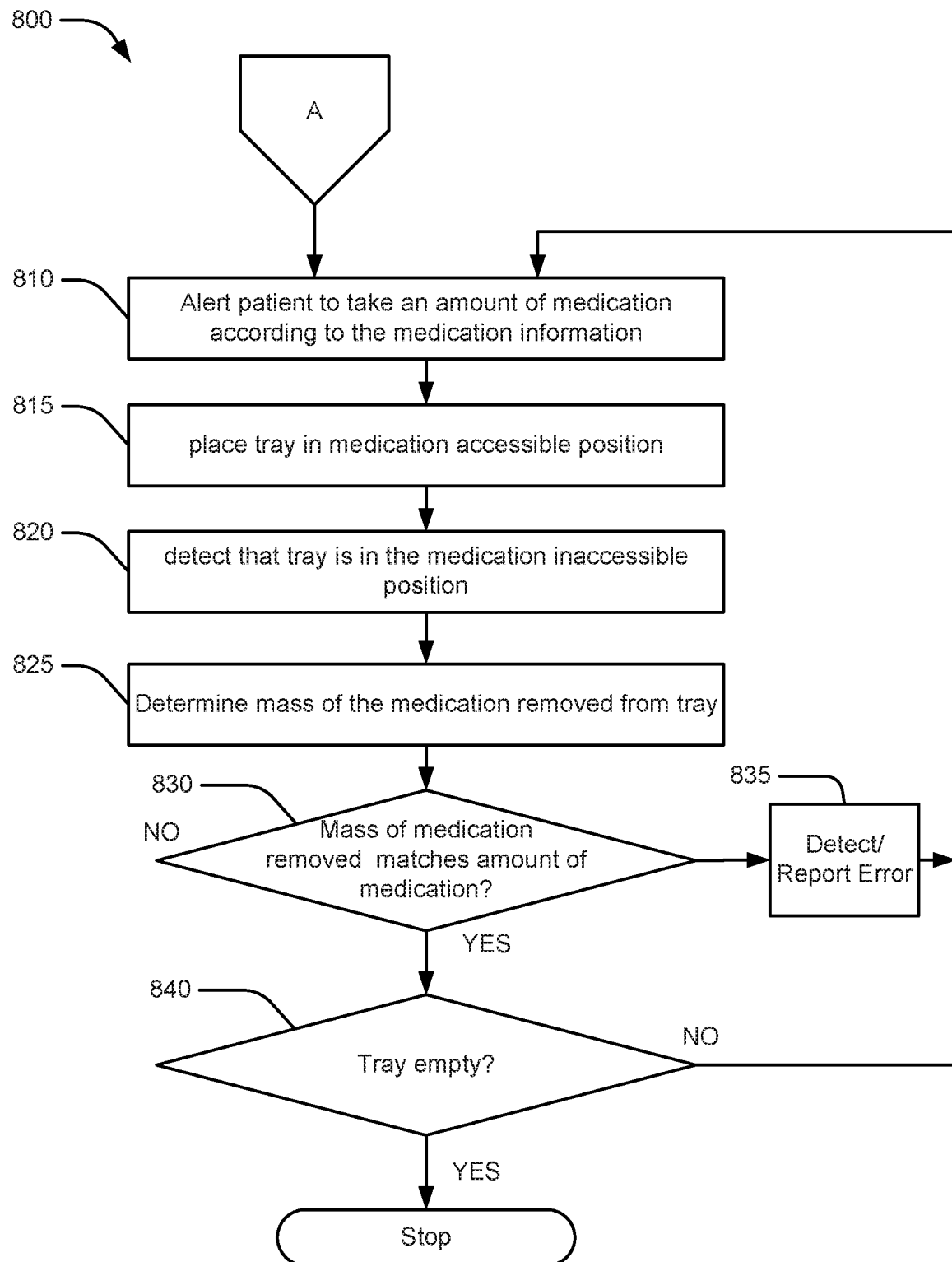
FIG. 11 is a flowchart illustrating an example method of dispensing medication from a medication dispensing device in accordance with aspects of the present disclosure.

FIG. 11 is a flowchart illustrating an example method 800 of dispensing medication from a medication dispensing device 20 (FIG. 1). In an aspect, the method 800 may be performed by a medication dispensing device 20 (FIG. 1). The method 800 may follow a similar method to the method 700 illustrated in FIG. 10.

In block 810, the method 800 may include alerting a patient to take an amount of medication according to the medication information. In an aspect, for example, the processor 410 (FIG. 7) may alert the patient via user interface 420 (FIG. 7) to take the amount of medication according to the medication information. For example, the amount of medication may be a single dose of the medication as indicated in the medication information. As another example, the patient may select multiple doses (e.g., for extended travel), and the processor 410 (FIG. 7) may determine an amount of medication for the multiple doses.

In block 815, the method 800 may include placing the tray in a medication accessible position. The block 815 may be similar to the block 720. In block 820, the method 800 may include determining that the tray is in the medication inaccessible condition. The block 820 may be similar to the block 725.

In block 825, the method 800 may include determining a mass/weight of the medication removed from the tray. In an aspect, for example, the processor 410 (FIG. 7) may determine the mass/weight of the medication removed from the tray based on a measurement from a corresponding load cell 460 (FIG. 7). For example, the processor 410 (FIG. 7) may receive a reading from the corresponding load cell 460 (FIG. 7) that includes a mass/weight of the tray and/or a medication container after the tray has returned to the medication inaccessible condition. The processor 410 may subtract a known mass/weight of the tray and/or medication container, for example, measured before placement of the tray in the medication accessible condition to determine the mass/weight of the medication removed from the tray.

In block 830, the method 800 may include determining whether the mass/weight of medication removed from the tray matches the amount of medication. In an aspect, for example, the processor 410 may determine whether the mass/weight of medication removed from the tray matches the amount of medication. For example, the processor 410 (FIG. 7) may compare the mass/weight of medication removed from the tray to the amount of medication. The processor 410 (FIG. 7) may compare the masses/weights directly, or convert the masses/weights into units of medication (e.g., pills). The processor 410 (FIG. 7) may use a tolerance to account for the precision of the load cell and slight variations in the mass/weight of individual units of medication. If the mass/weight of medication removed from the tray substantially matches the amount of medication, the method 800 may proceed to the block 840. If the mass/weight of medication removed from the tray does not substantially match the amount of medication, the method 800 may proceed to the block 835.

In block 835, the method 800 may include detecting, reporting, and/or correcting possible errors. In an aspect, for example, the processor 410 (FIG. 7) may determine that an error may have occurred because the mass/weight of medication removed from the tray does not match the amount of medication. The processor 410 (FIG. 7) may report the error to another device (e.g., a server) on the network 40 (FIG. 1) via the network interface 425 (FIG. 7). Further, the processor 410 (FIG. 7) may attempt to correct or otherwise address the error. In an aspect, the processor 410 (FIG. 7) may instruct a patient or other user to take remedial action. For example, the processor 410 (FIG. 7) may control the user interface 420 (FIG. 7) to provide information about the possible error. A message may be provided via the user interface 420 (FIG. 7) requesting input to confirm the number of units of medication removed from the tray, for example. The user interface 420 (FIG. 7) may provide an instruction to take additional medication from the tray or return units of medication to the tray. For example, the method 800 may return to block 810. The user interface 420 (FIG. 7) may also display warnings regarding taking insufficient or excessive doses of the medication, for example. Further, the user interface 420 may allow the patient or other user to indicate if there was a problem with the medication (e.g., dropped, lost, damaged). Any error information may be used to update medication information or patient information. Further, the network 40 may reschedule a patient's pharmacy refill date based on any errors.

In block 840, the method 800 may include determining whether the tray is empty. In an aspect, for example, the processor 410 (FIG. 7) may determine whether the tray is empty based on the measured mass/weight of medication. If the tray is empty, the user interface 420 may instruct a patient or other user to remove an empty medication container. The user interface 420 may also instruct the user to insert a new medication container. For example, the method 800 may return to the method 700. Alternatively, the method 800 may end. If the tray is not empty, the method 800 may return to block 810 to dispense a second medication, or to dispense another dose of the medication at the next dosage time according to the medication information, for example.

Figure 12:
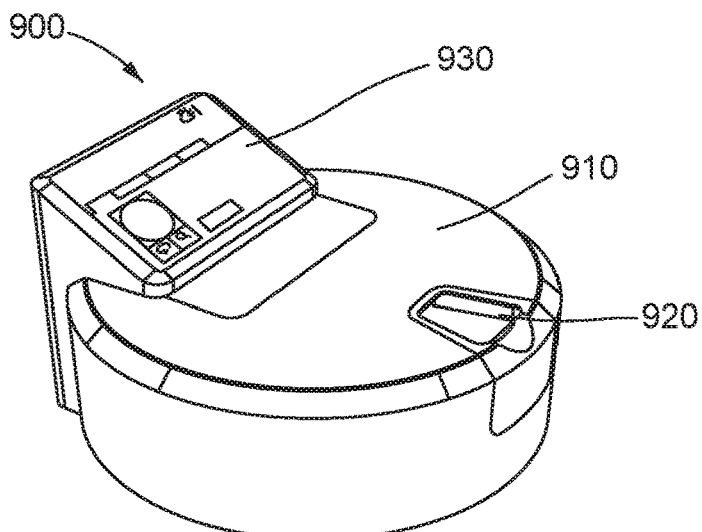
FIG. 12 illustrates another example medication dispensing device in accordance with aspects of the present disclosure.

FIG. 12 illustrates another example medication dispensing device 900. The medication dispensing device 900 may include a main body 910 including a single opening 920 for accessing an internal medication tray. The medication tray may include a plurality of medication holders, each of which may contain medication or store a medication container. The medication dispensing device 900 may include a control system 400. The user interface 930 may correspond to the user interface 420 (FIG. 7). The control system 400 (FIG. 7) may rotate the medication tray such that a selected medication holder aligns with the opening 920 to place the tray in a medication accessible condition for the medication holder. A single load cell 560 (FIG. 7), for example, may determine the mass/weight of the entire tray, including a plurality of medications stored in respective medication holders. The processor 410 (FIG. 7) may determine the mass/weight of individual medications based on changes in the mass/weight when a respective medication holder is in the medication accessible position.

Figure 13:
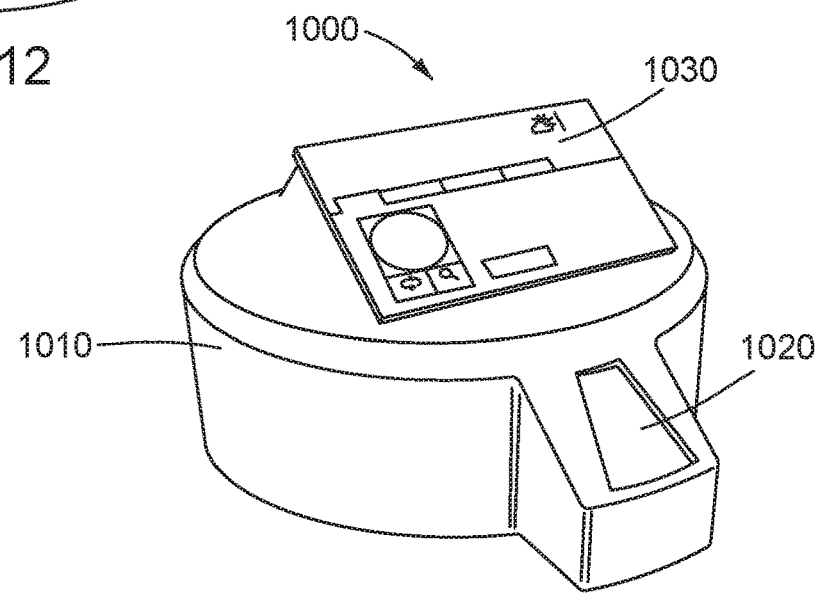
FIG. 13 illustrates another example medication dispensing device in accordance with aspects of the present disclosure.

FIG. 13 illustrates another example medication dispensing device 1000. The medication dispensing device 1000 may include a main body 1010, including an opening 1020. The medication tray may be similar to the medication tray of the example devices that include a plurality of medication holders, which may each contain medication or store a medication container. The medication dispensing device 1000 may further include an actuator configured to lift a medication holder or medication container out of the tray and toward the opening 1020, for example. The actuator may include a hydraulic or pneumatic cylinder, solenoid, threaded shaft, or arm, for example. The medication dispensing device 1000 may also include a control system 400. The controller 440 may be further configured to control the actuator.

Figure 14:
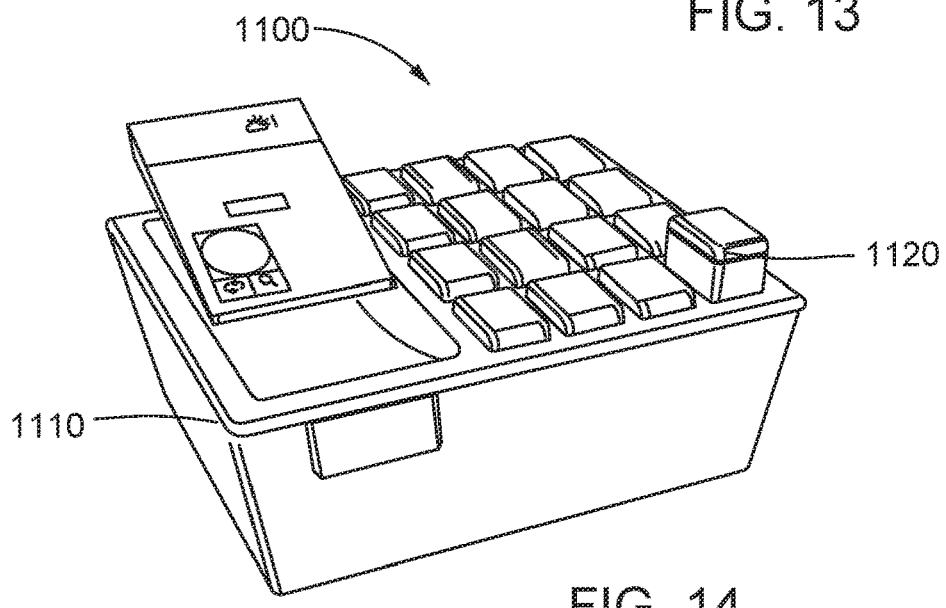
FIG. 14 illustrates another example medication dispensing device in accordance with aspects of the present disclosure.

FIG. 14 illustrates another example medication dispensing device 1100. The medication dispensing device 1100 may include a main body 1110. Instead of a rotating tray, the medication dispensing device 1100 may include a plurality of individual medication holders 1120. Each individual medication holder 1120 may be controlled by an individual actuator to open a door covering the medication holder 1120, for example, and/or lift the medication holder 1120 to a medication accessible position. Further, each medication holder 1120 may include a load cell to measure a mass/weight of medication in the medication holder 1120. The medication dispensing device 1100 may also include a control system 400 (FIG. 7). The controller 440 (FIG. 7) may be further configured to control the actuator for each medication holder 1120, for example.

Figure 15:
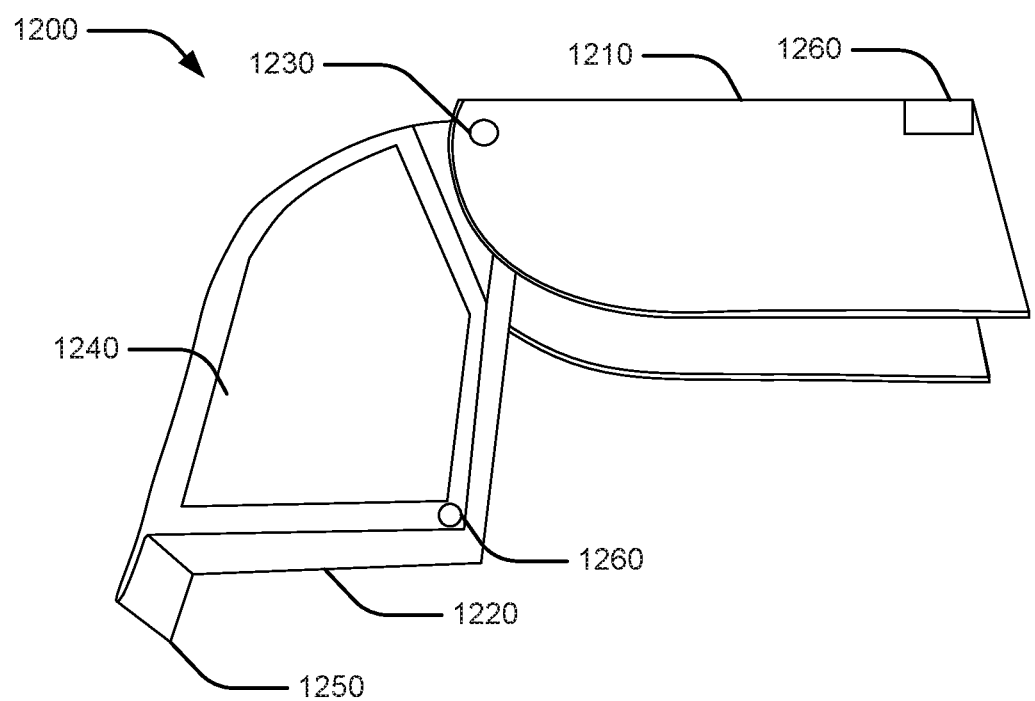
FIG. 15 illustrates an example of a medication holder in accordance with aspects of the present disclosure.
Figure 16:
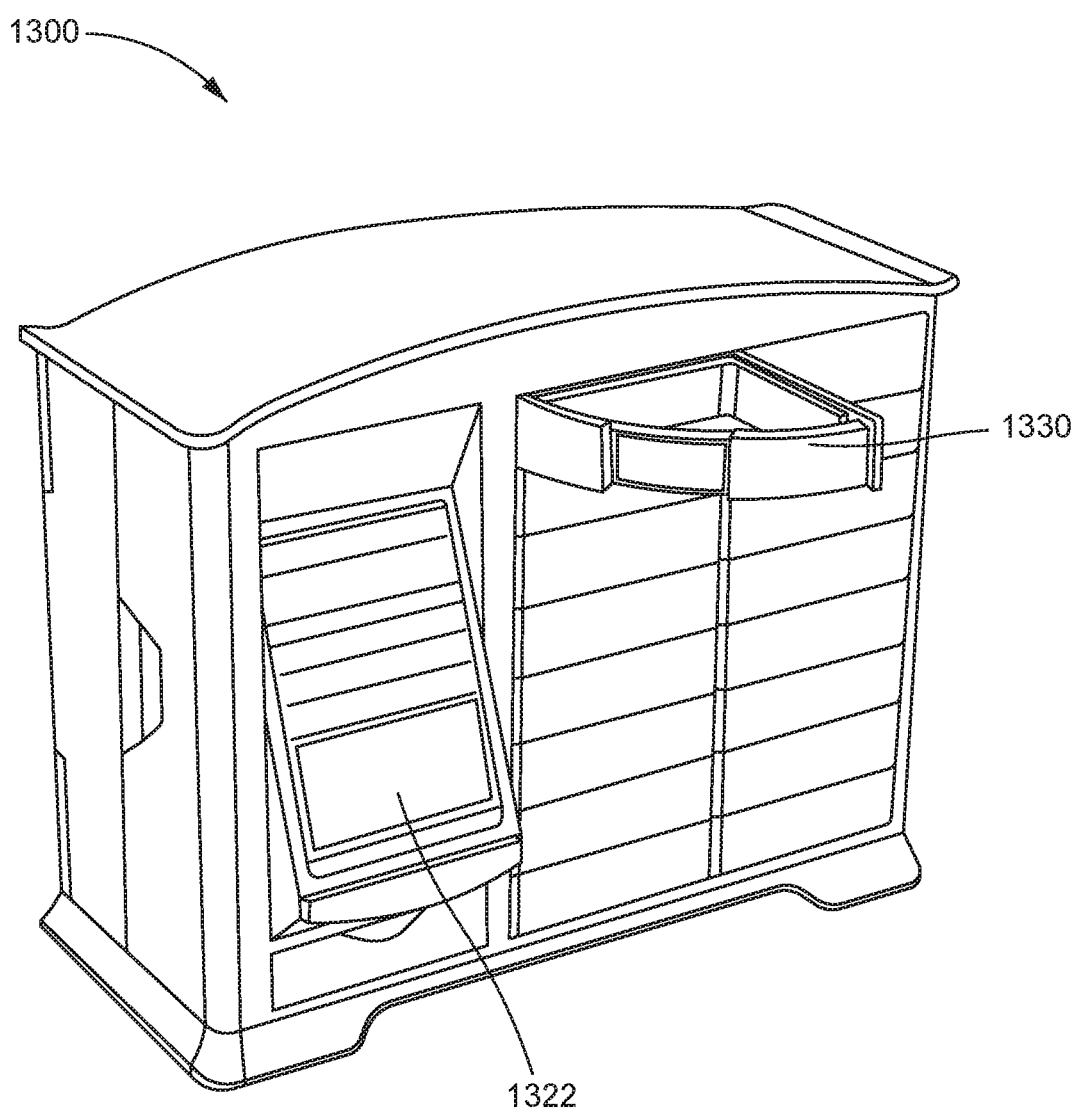
FIG. 16 illustrates another example of a medication dispensing device in accordance with aspects of the present disclosure.

FIG. 15 illustrates another example of a medication holder 1200. A plurality of medication holders 1200 may be arranged within a main body of a medication dispensing device. For example, a plurality of medication holders 1200 may replace the trays 230a-e in the medication dispensing device 200 in FIG. 2. The medication holder 1200 may include a housing 1210 pivotably connected to a pan 1220 by a hinge 1230, for example. The housing 1210 may be located within or integrally formed with a main body of a medication dispensing device 200 (FIG. 2). The pan 1220 may include a bowl 1240 for storing medication and a tab 1250 for gripping the pan 1220, for example. The bowl 1240 may have a sloped or curved bottom surface similar to the bowl 330 (FIG. 5A), for example. In another aspect, the bowl 1240 may receive a medication container similar to medication container 300 (FIG. 5A), for example. The medication holder 1200 may further include a biasing element, such as a spring (not shown) configured to bias the medication holder 1200 into a medication accessible position as illustrated in FIG. 15. A processor 410 (FIG. 7) or controller 440 (FIG. 7) may place the medication holder 1200 into a medication accessible position by releasing a lock 1260, for example. A user may manually place the medication holder 1200 into a medication inaccessible position by pressing on the tab 1250.

FIG. 14 illustrates another example medication dispensing device 1300. The example medication dispensing device 1300 may include a plurality of trays 1330. Each tray 1330 may be formed so as to be readily received in a medication holder 1200 (FIG. 13). The trays 1330 may be arranged in one or more vertical columns. Each individual tray 1330 may be controlled by an individual actuator, for example, to control lock 1260 (FIG. 13) to move the pan 1220 (FIG. 13) to a medication accessible position. Further, each tray 1330 may include a load cell to measure a mass/weight of medication in the tray 1330. The user interface 1322 may be similar to the user interface 22 (FIG. 1) or user interface 222 (FIGS. 2, 3). The medication dispensing device 1300 may also include the control system 400 (FIG. 7). The controller 440 (FIG. 7) may be further configured to control the actuator for each tray 1330.

While the foregoing disclosure discusses example aspects and/or features, it should be noted that various changes and modifications could be made herein without departing from the scope of the described aspects and/or features as defined by the appended claims. Furthermore, although elements of the described aspects and/or features may be described or claimed in the singular, the plural is contemplated unless limitation to the singular is explicitly stated. Additionally, all or a portion of any aspect and/or embodiment may be utilized with all or a portion of any other aspect and/or feature, unless stated otherwise.

What is claimed is:

1. A medical dispensing device, comprising:
    a plurality of trays, each tray including a load cell to measure a mass of a medication contained in each tray, each tray being placeable in a medication accessible position and a medication inaccessible position;
    a user interface that provides for user input and instructions to the user to operate and access each medication; and
    a computer server communicatively coupled to the user interface and comprising a processor, wherein the computer server receives and stores information input by a user concerning a medication, and, in response to receiving instructions to provide access to the medication, the processor provides instructions to:
    obtain a first mass measurement of the medication in a tray;
    transition the tray containing the medication from the medication inaccessible position to the medication accessible position;
    transition the tray from the medication accessible position back to the medication inaccessible position;
    obtain information comprising a second mass measurement of the medication in the tray after the tray is transitioned from the medication accessible position back to the medication inaccessible position;
    determine, based on any change in the mass of the medication between the first mass measurement and the second mass measurement, whether any amount of the medication is removed from the tray; and
    if an amount of medication is determined to be removed from the tray, responsively calculate the mass of removed medication and determine whether the mass of removed medication matches a prescribed medication dose.

2. The medication dispensing device of claim 1, wherein the plurality of trays are arranged on a vertical axis and are movable horizontally between the medication accessible position and the medication inaccessible position.

3. The medication dispensing device of claim 1, wherein each tray is configurable to receive a medication container including an indicia, the medication dispensing device including a scanner configured to read the indicia.

4. The medication dispensing device of claim 3, wherein the indicia indicates a mass per unit of medication, and the processor determines a number of units of medication removed from the tray.

5. The medication dispensing device of claim 3, wherein the indicia indicates an initial mass of the medication, and the processor verifies that the medication container includes the initial mass of the medication.

6. The medication dispensing device of claim 3, wherein each of the plurality of trays comprises:
    a structural tray rotatably mounted to a vertical rod at the vertical axis; and
    a container receptacle including at least one container port configured to receive the medication container, wherein the load cell is mounted between the structural tray and the container receptacle.

7. The medication dispensing device of claim 3, further comprising a tray divider positioned between two of the trays such that the tray divider closes a medication container in a bottom one of the two trays when the bottom tray is in the medication inaccessible position.

8. The medication dispensing device of claim 3, wherein each tray comprises a first container port and a second container port, each container port capable of receiving a medication container.

9. The medication dispensing device of claim 8, wherein each tray is rotatable between the medication accessible position, the medication inaccessible position, and a second medication accessible position, wherein a medication container in the first container port is open in the medication accessible position and a medication container in the second container port is open in the second medication accessible position.

10. The medication dispensing device of claim 8, further comprising a motor, operable by the controller to rotate at least one of the plurality of trays between the medication accessible position, the medication inaccessible position, and the second medication accessible position.

11. The medication dispensing device of claim 8, wherein the scanner is positioned to read an indicia of a medication container in the second container port when the tray is in the second medication accessible position.

12. The medication dispensing device of claim 3, wherein the scanner is positioned to read the indicia when the tray is in the medication inaccessible position.

13. The medication dispensing device of claim 12, further comprising a mirror positioned to reflect an image of the indicia to the scanner when the tray is in the medication inaccessible position.

14. The medication dispensing device of claim 3, wherein at least one of the trays includes a second indicia readable by the scanner when the medication container tray does not include a container, the second indicia indicating that the medication container tray is empty.

15. The medication dispensing device of claim 3, wherein the medication dispensing container has a sloped surface facilitating removal of the medication.

16. The medication dispensing device of claim 1, further comprising a peripheral device configured to obtain a biometric reading from a patient, wherein the user interface instructs a user to use the peripheral device and the processor reports the biometric reading to a network application.

* * * * *